(12) United States Patent
Dabrowiak et al.

(10) Patent No.: US 11,497,648 B2
(45) Date of Patent: Nov. 15, 2022

(54) ADVANCED SYSTEMS AND METHODS FOR PATIENT BODY TEMPERATURE CONTROL

(71) Applicant: Zoll Circulation, Inc., San Jose, CA (US)

(72) Inventors: Jeremy Thomas Dabrowiak, Santa Clara, CA (US); Gary A. Freeman, Waltham, MA (US)

(73) Assignee: ZOLL Circulation, Inc., San Jose, CA (US)

( * ) Notice: Subject to any disclaimer, the term of this patent is extended or adjusted under 35 U.S.C. 154(b) by 1034 days.

(21) Appl. No.: 15/594,539

(22) Filed: May 12, 2017

(65) Prior Publication Data

US 2018/0325725 A1   Nov. 15, 2018

(51) Int. Cl.
*A61F 7/12* (2006.01)
*A61F 7/00* (2006.01)

(52) U.S. Cl.
CPC .............. *A61F 7/12* (2013.01); *A61F 7/0085* (2013.01); *A61F 7/123* (2013.01); *A61F 2007/0054* (2013.01); *A61F 2007/0093* (2013.01); *A61F 2007/0096* (2013.01); *A61F 2007/126* (2013.01)

(58) Field of Classification Search
CPC .......... A61F 7/12; A61F 7/0085; A61F 7/123; A61F 2007/0054; A61F 2007/0093; A61F 2007/0096; A61F 2007/126; A61F 2007/002; A61F 2007/0059; A61F 2007/0295
See application file for complete search history.

(56) References Cited

U.S. PATENT DOCUMENTS

| | | | |
|---|---|---|---|
| 6,309,350 B1 | 10/2001 | VanTassel et al. | |
| 6,589,271 B1 | 7/2003 | Tzeng | |
| 7,087,026 B2 * | 8/2006 | Callister | A61B 5/029 600/504 |
| 7,510,569 B2 * | 3/2009 | Dae | A61F 7/123 607/105 |
| 9,492,633 B2 | 11/2016 | Dabrowiak | |
| 2004/0267339 A1 | 12/2004 | Yon et al. | |
| 2013/0030411 A1 | 1/2013 | Kreck | |
| 2013/0079855 A1 | 3/2013 | Helkowski et al. | |
| 2013/0079856 A1 | 3/2013 | Dabrowiak et al. | |
| 2013/0090708 A1 | 4/2013 | Dabrowiak et al. | |
| 2013/0178923 A1 | 7/2013 | Dabrowiak | |
| 2014/0058484 A1 * | 2/2014 | Callister | G05D 23/1925 607/105 |
| 2014/0094880 A1 | 4/2014 | Lim et al. | |
| 2014/0094882 A1 | 4/2014 | Lim | |
| 2014/0094883 A1 | 4/2014 | Lim et al. | |
| 2015/0257926 A1 | 9/2015 | Brian, III et al. | |

(Continued)

FOREIGN PATENT DOCUMENTS

WO    WO2004023982 A2    3/2004

OTHER PUBLICATIONS

PCT International Search Report dated May 1, 2018 in related PCT Application No. PCT/US2018/016755.

(Continued)

*Primary Examiner* — Joanne M Hoffman
*Assistant Examiner* — Christine A Dedoulis
(74) *Attorney, Agent, or Firm* — Zoll Circulation, Inc.

(57) ABSTRACT

Devices, systems and methods for controlling the temperature of all or part of the body of a human or animal subject.

21 Claims, 22 Drawing Sheets

(56) References Cited

U.S. PATENT DOCUMENTS

| | | | |
|---|---|---|---|
| 2015/0282786 A1* | 10/2015 | Anand | A61B 8/5215 |
| | | | 600/438 |
| 2016/0135987 A1* | 5/2016 | Mignot | A61B 34/10 |
| | | | 607/105 |
| 2018/0185192 A1 | 7/2018 | Mazzone et al. | |
| 2018/0185193 A1 | 7/2018 | Mazzone et al. | |
| 2018/0207024 A1 | 7/2018 | Dabrowiak et al. | |
| 2018/0214302 A1 | 8/2018 | Dabrowiak et al. | |
| 2018/0214303 A1 | 8/2018 | Dabrowiak et al. | |

OTHER PUBLICATIONS

Extended European Search Report in Application No. 18798947.0, dated Dec. 11, 2020, 11 pages.

* cited by examiner

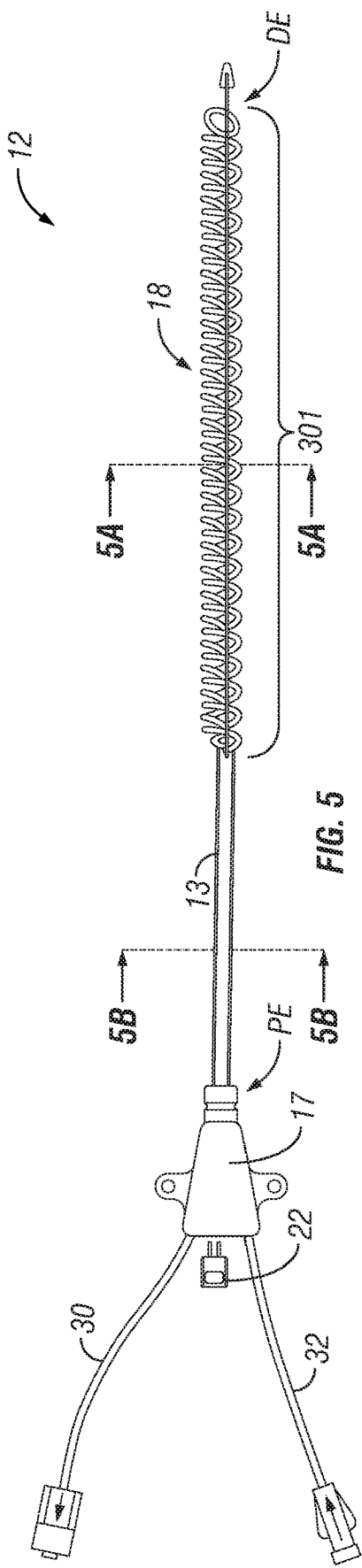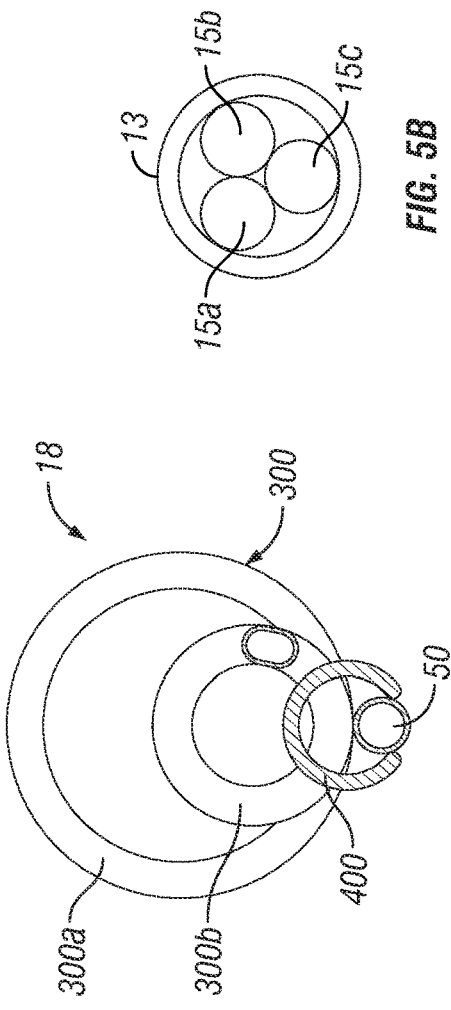

| Initiate Anti-shivering Medication Protocol | Turn on Endovascular Heat Exchange System |
|---|---|
| Begin Therapeutic Hypothermia with Intravenous Infusion of up to One Liter of 4 degree C Saline Solution Using Pressure Bag, Then Continue Using Endovascular Heat Exchange System | |

*Documentation/Work Up:*

| Document Time Endovascular Heat Exchange System Was Turned On | Document Time of Occurrence of STEMI, Arrival Time at E. D. and Other Subject Data Upon Arrival (e.g., Temperature, Physical Exam, Vital Signs, Blood Studies, Lab Studies, Cardiac Markers, Troponin T, 12-Lead ECG) | Maintain Sedation and Document All Medications |
|---|---|---|

*Initiation of Cooling to 32 Degrees C:*

| Begin cooling induction by forced infusion 2SmL/kg 4-C saline for up to 1 L at treating physician's discretion | Insert heat exchange catheter and connect to cassette in heat exchange console. Enter 32 degree C target body temperature and cool at maximum power. Insert temperature probe. | Use Bair Hugger™ System for counter warming of body surface and follow hospital guidelines for venous thromboembolism prophylaxis |
|---|---|---|

*FIG. 23*

If BSAS≥2.2 at 32.0·C increase dose of Pethidine as indicated in Antishivering Guidelines (Attachment II) and increase set-point temperature to 32.5·C

*Immediately Prior to Reperfusion:*

Perform Angiogram after Induction of Hypothermia and just prior to PCI | Document Core Body Temp. at time of PCI & Continue Cooling until subject has reached 32.0±1.0·C

*Maintenance of Hypothermia at Target Temperature of 32.0 +/- 1.0 degrees C:*

Maintain Target Temperature of 32.0 +/- 1.0 degrees C for 3.0 Hours +/- 15 Minutes | Assess Need for Antishivering Medication

*Rewarming:*

Increase Target Temperature to 36.0 degrees C and rewarm at a rate of 1.0 degree C per hour until subject's body temp is 36.0 degrees C | Assess Need for Antishivering Medication

*Catheter Removal:*

Remove heat exchange catheter and temperature probe. Dispose per guidelines

FIG. 23
*(Cont'd)*

ADVANCED SYSTEMS AND METHODS FOR PATIENT BODY TEMPERATURE CONTROL

FIELD OF THE INVENTION

The present disclosure relates generally to the fields of medicine and engineering and more particularly to devices, systems and methods for controlling the temperature of a human or animal subject.

BACKGROUND

Pursuant to 37 CFR 1.71(e), this patent document contains material which is subject to copyright protection and the owner of this patent document reserves all copyright rights whatsoever.

Hypothermia can be induced in humans and some non-human animals for the purpose of protecting various organs and tissues against the effects of ischemic, anoxic or toxic insult. Studies have shown that induced hypothermia in a subject suffering from an evolving myocardial infarction can, in at least some cases, limit the size and severity of the infarct. For example, in at least one study, it was observed that patients with anterior wall infarctions whose core body temperature had been lowered to at least 35° C. prior to reperfusion by angioplasty had significantly smaller median infarct size than other patients with anterior wall infarctions whose core body temperature was greater than 35° C. at the time of reperfusion. This observation is not explained by other factors such as time-to-presentation, lesion location or quantity of antegrade coronary flow (TIMI Flow) prior to the angioplasty. This would suggest that, at least in acute myocardial infarction (AMI) cases, lowering of the patient's core body temperature to at least 35° C. prior to reperfusion of the ischemic myocardium may have beneficial effects.

SUMMARY

Methods and systems for warming or cooling a subject, e.g., a target location within a subject's vasculature, to a target temperature are provided herein. A system may comprise at least one heat exchanger useable to exchange heat with the subject's flowing blood at a heat exchange location different from the target location. Such method and system further comprises at least one temperature sensor positioned and useable to sense body temperature(s) at one or more temperature sensing location(s) in or on the subject's body, such temperature sensing location(s) being different from the target location. Such method and system further comprises a controller which receives signals from the temperature sensor(s) indicating the temperature being sensed at the temperature sensing location(s) and, based on said signals, controls the heat exchanger to warm or cool blood flowing through the heat exchange location, as needed, to result in warming or cooling of the target location and/or all or part of the subject to the target temperature. The controller may comprise a processor programmed to estimate the temperature at the target location based on the temperature sensed at the temperature sensing location. In some embodiments the controller may alter the temperature sensed at the sensing location by adding or subtracting a correction factor which is based on historical data or a known expected temperature difference between the sensing location and the target location. In other embodiments, the controller may be programmed to perform more complex operations and/or to apply algorithms which estimate the temperature at the target location, examples of which are described herein. In some embodiments, the controller may estimate the temperature at the target location in either current time or in real time, based on the temperature sensed at the temperature sensing location at the current time or in real time, and based on the estimated temperature at the target location.

The temperature sensing location(s) may be at any suitable locations in or on the subject's body. Examples of useable temperature sensing locations include locations in the inferior vena cava, superior vena cava, pulmonary artery, renal vein and hepatic vein.

The methods and systems in certain embodiments may be used to effect a controlled degree of therapeutic hypothermia, e.g., at a target location (e.g., the left ventricle of the heart) to deter or lessen damage from an insult (e.g., infarct, hypoxic insult, toxic insult, ischemic insult, etc.) at the target location or of the subject as a whole.

Further aspects and details of the present invention will be understood upon reading of the detailed description and examples set forth herebelow.

BRIEF DESCRIPTION OF THE DRAWINGS

The following detailed description and examples are provided for the purpose of non-exhaustively describing some, but not necessarily all, examples or embodiments of the invention, and shall not limit the scope of the invention in any way.

FIG. 5 shows the heat exchange catheter of the system of FIG. 1.

FIG. 5A is a cross-sectional view through line 5A-5A of FIG. 5.

FIG. 5B is a cross-sectional view through line 5B-5B of FIG. 5.

FIG. 6A is a side view of the elongate member; FIG. 6B is a side view of the heat exchange tube and FIG. 6C is a side view of an optional elongate luminal member and the distal tip member.

FIG. 23 is a flow diagram showing one embodiment of a process for using a heat exchange catheter system to deter reperfusion injury in a subject who is suffering from an ischemic event that is treatable by a reperfusion procedure or administration of a reperfusion agent (e.g., thrombolytic drug).

DETAILED DESCRIPTION

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

Figure 1:
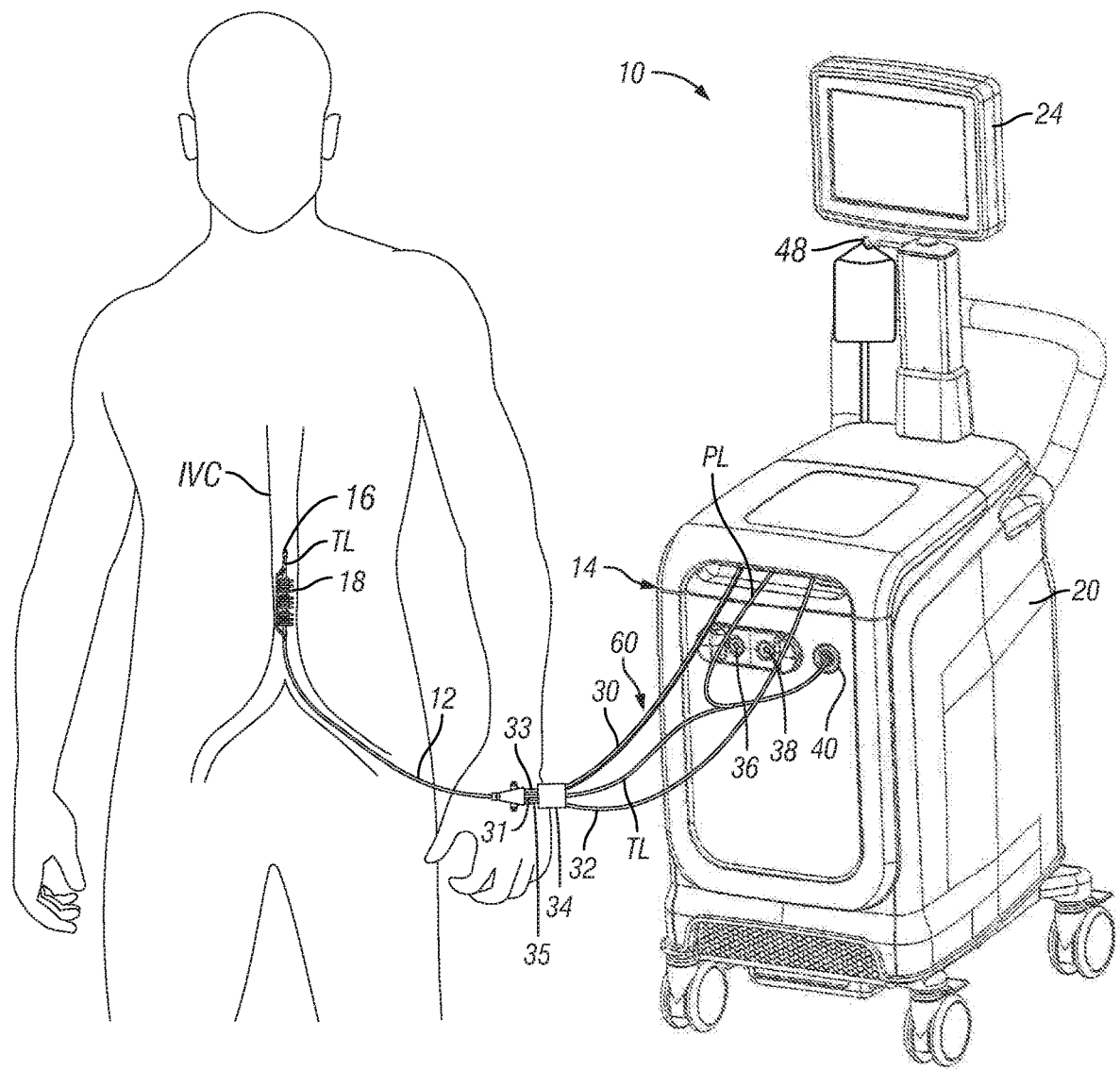
FIG. 1 shows an example of a heat exchange catheter system which generally comprises a control console, tubing/cassette/sensor module assembly and heat exchange catheter, useable for practicing some embodiments described herein.

The drawings include showings of certain organs and other anatomical structures, which are labeled as follows:

Aorta . . . A
Heart . . . H
Right Atrium . . . RA
Left Atrium . . . LA
Right Ventricle . . . RV
Left Ventricle . . . LV
Pulmonary Artery . . . PA
Superior Vena Cava . . . IVC
Inferior Vena Cava . . . IVC
Femoral Vein . . . FV
Left Renal Vein . . . LRV
Right Renal Vein . . . RRV
Hepatic Veins . . . HV FIG. 1 shows an example of a endovascular temperature management system 10 which generally comprises an endovascular heat exchange catheter 12, an extracorporeal control console 14 and a tubing/cassette/sensor module assembly 60. Additionally, at least one body temperature sensor 16 is connected by way of a temperature lead TL, or alternatively by wireless connectivity, to the controller 36. In the non-limiting example of FIG. 1, the heat exchange catheter 12 has been inserted into the vasculature of a subject and advanced to a position where its heat exchanger 18 is in the subject's inferior vena cava IVC. A temperature lead TL having a temperature sensor TS temperature sensor 16 is inserted through a lumen of the heat exchange catheter 12 and advanced out of the distal end of the catheter 12 to a temperature sensing location TSL that is also in the subject's inferior vena cava IVC. As described elsewhere in this patent application, in some embodiments, a plurality of temperature sensors 16 may be employed.

The catheter 12, tubing/cassette/sensor module assembly 60 or cassette assembly and temperature lead/sensor 16 may be disposable items intended for a single use, while the control console 14 may be a non-disposable device intended for multiple uses.

In the embodiment shown, the endovascular heat exchange catheter 12 comprises an elongate catheter body which has a heat exchanger 18 positioned thereon. Inflow and outflow lumens (not shown) are present within the catheter body 16 to facilitate circulation of a thermal exchange fluid (e.g., sterile 0.9% sodium chloride solution or other suitable thermal exchange fluid) through the heat exchanger 18. Optionally, the catheter may also include a working lumen (not shown in FIG. 1) which extends through the catheter body 16 and terminates distally at an opening in the distal end of the catheter body 16. Such working lumen may serve as a guidewire lumen to facilitate insertion and position of the catheter 12 and/or may be used after insertion of the catheter 12 for delivery of fluids, medicaments or other devices. For example, as shown in FIG. 1, in some embodiments, the temperature sensor 16 may be inserted through the catheter's working lumen and advanced out of the distal end opening to a location beyond the distal end of the catheter 12. Alternatively, in other embodiments, the temperature sensor TS may be positioned at various other locations on or in the subject's body to sense the desired body temperature(s).

The extracorporeal control console 14 generally comprises a main housing 20 and a console head 24. As described in detail herebelow, the main housing 20 contains various apparatus and circuitry for warming/cooling thermal exchange fluid to controlled temperature(s) and for pumping such warmed or cooled thermal exchange fluid through the catheter 18 to effectively modify and/or control the subject's body temperature. The console head 24 comprises a display device or user interface 38, such as a touch screen system, whereby certain information may be input by, and certain information may be displayed to, users of the system 10. On the housing 20 there are provided a first connection port 40 for connection of a temperature sensor TS that is inserted through the heat exchange catheter 12 as shown in FIG. 1 as well as other connection ports 36, 38 for connection of additional or alternative types of temperature sensors and/or other apparatus.

Figure 2:
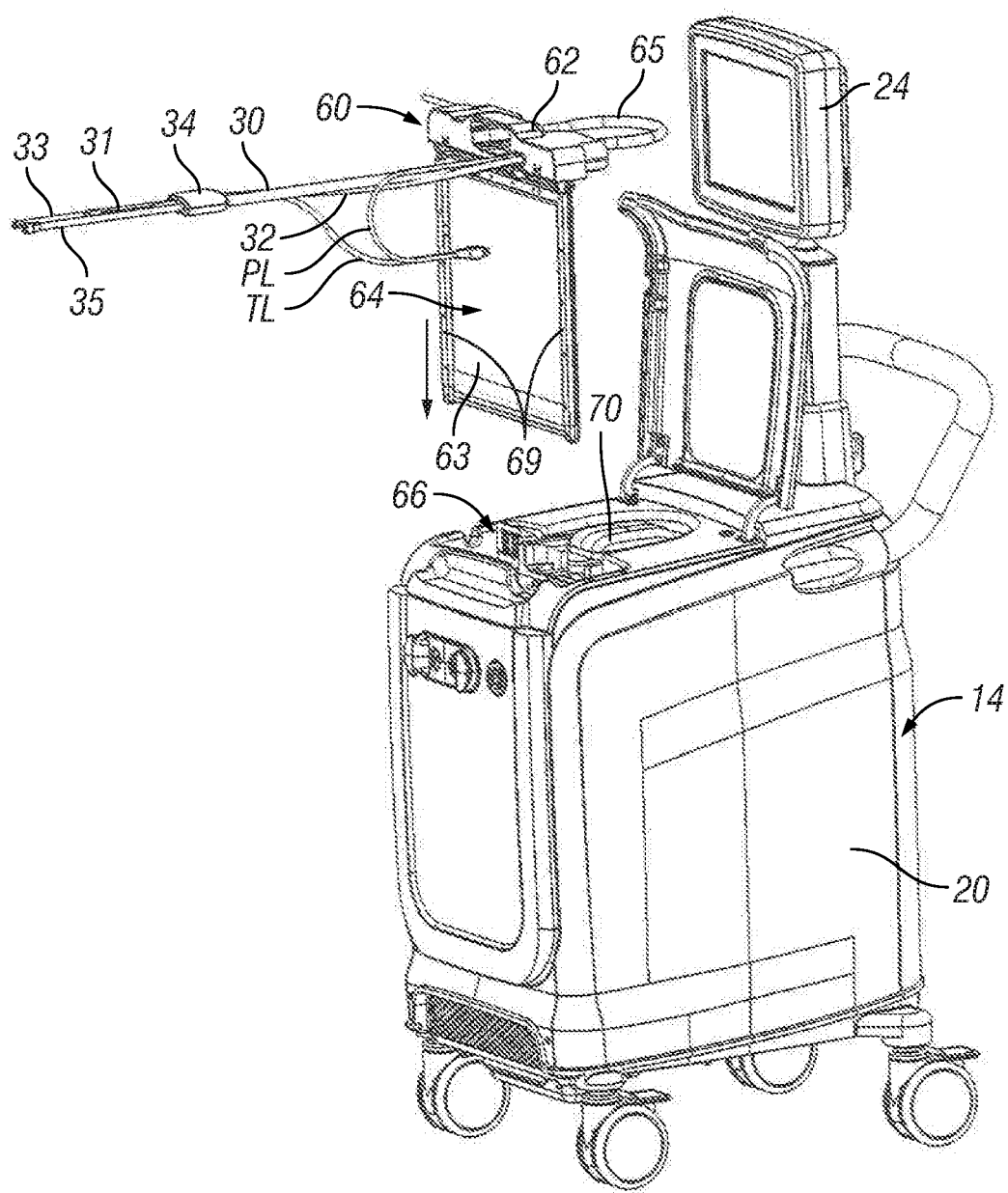
FIG. 2 is an exploded view of the control console with its access cover in an open position and the tubing/cassette/sensor module assembly staged for insertion in, and operative connection to, the control console.

As may be appreciated from the showing of FIG. 2, the tubing/cassette/sensor module assembly 60 generally comprises a sensor module 34, an inflow conduit 32, inflow connector 33, outflow conduit 30, outflow connector 31, temperature lead connector 40, pressure lead PL, cassette 64, cassette housing 62 and peristaltic pump tubing 65.

Figure 3:
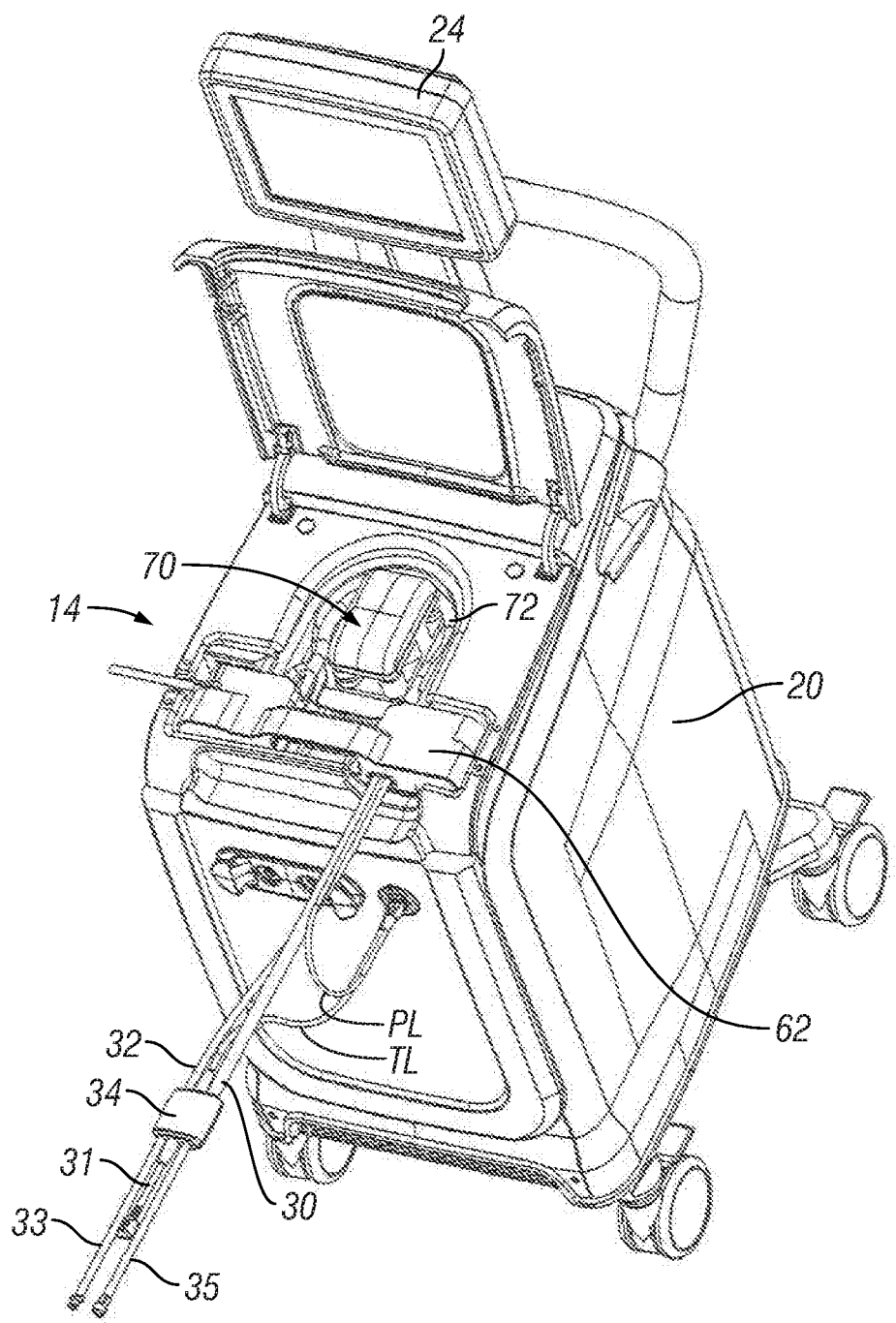
FIG. 3 is a top (perspective) view of the control console with its access cover in an open position and the tubing/cassette/sensor module assembly operatively inserted in and connected to the control console.
Figure 4:
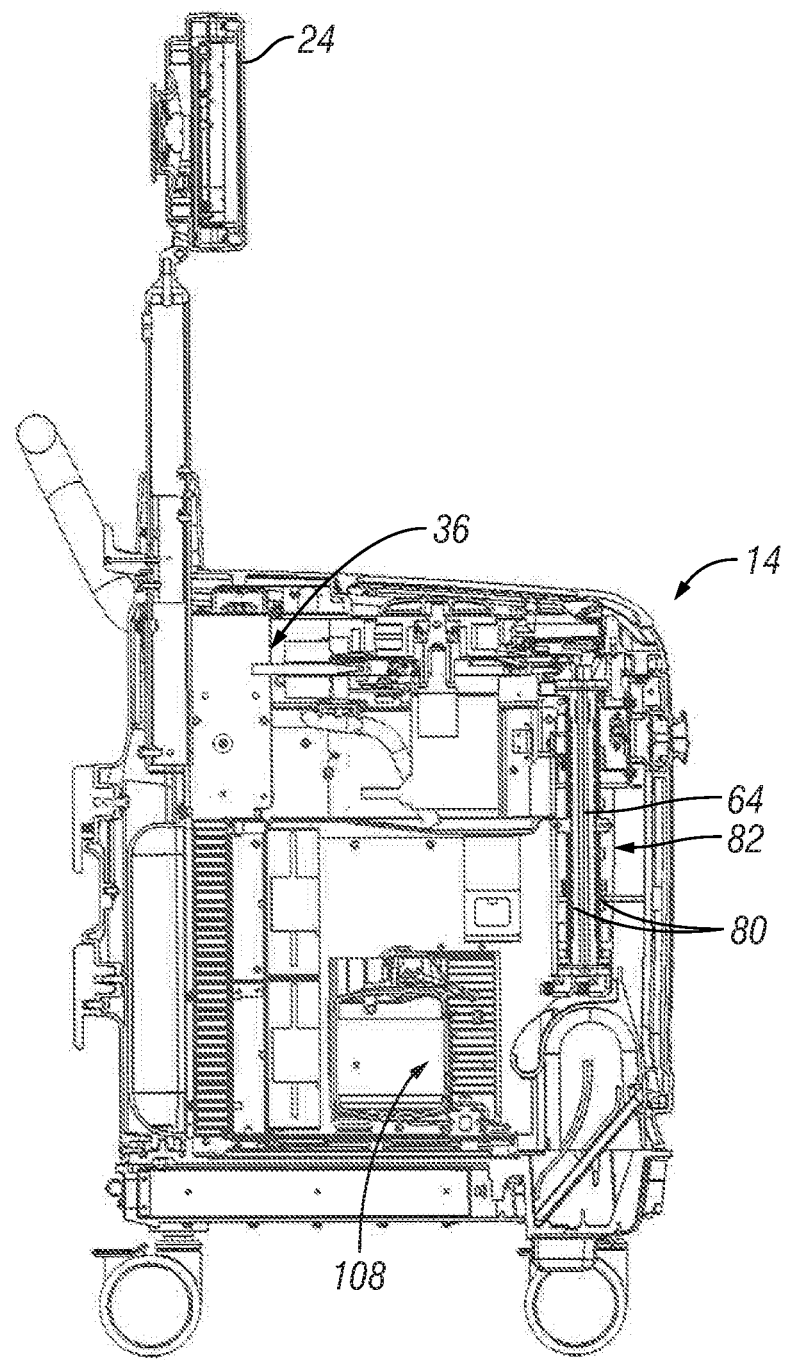
FIG. 4 is a right cross-sectional view of the control console.

As shown in FIGS. 3 and 4, the cassette 64 of the tubing/cassette/sensor module assembly 60 is inserted through an openable/closable access cover 42 of the control console 14 and into a cassette receiving space 66 positioned between thermal exchange plates 80 and the pump tubing 65 is insertable into a tubing raceway 72 of pump 70.

With reference to FIG. 4, a thermal exchange engine 108 within the control console 14 includes a refrigeration system for cooling fluid that circulates through the thermal exchange plates 80 when the system is operating in cooling mode and resistance heaters 82 for warming the thermal exchange plates 80 when the system is operating in warming mode.

The control console 14 also includes a programmable controller 36 and user interface 24, such as a liquid crystal display (LCD), e.g., touchscreen, which is in communication with the controller 36. The user interface displays system information and also receives user input as well as sensor data, as described more fully herein.

Further details of the control console 14, tubing/cassette/sensor module assembly 60 or cassette assembly and temperature lead TL/temperature sensor 16 are described in copending U.S. patent application Ser. No. 15/423,581 entitled Devices, Systems and Methods for Endovascular Temperature Control, the entire disclosure of which is hereby expressly incorporated herein by reference.

Figure 6A:
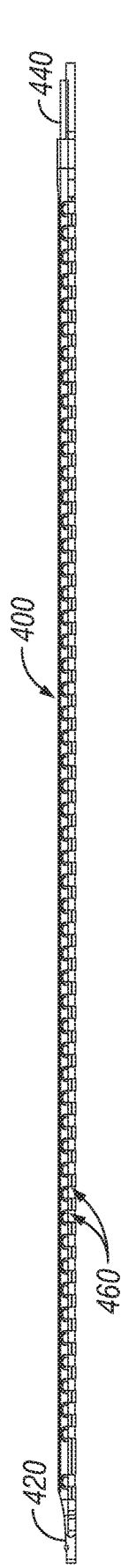
FIGS. 6A through 6C show certain components of the endovascular heat exchange catheter embodiment of FIG. 2. Specifically.
Figure 6B:
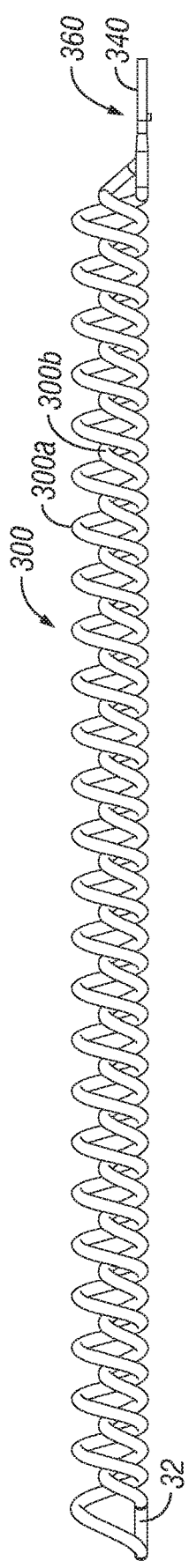
Figure 6C:
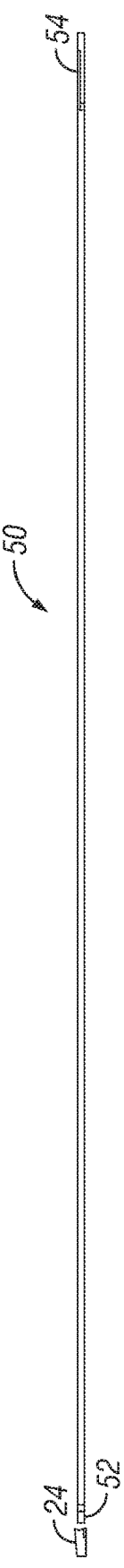

With reference to FIGS. 5 through 6C, the heat exchange catheter 12 of the system shown in FIG. 1 generally comprises a proximal catheter body 13 and an assembly which comprises the heat exchanger 18 attached to and/or extending distally from the proximal catheter body 13. In this particular embodiment, the proximal catheter body 13 has three lumens, an inflow lumen 15a, an outflow lumen 15b and an optional through lumen 15c. A hub 17 is mounted on the proximal end PE of the proximal catheter body 13. The hub 17 has an inflow connector 30 that is connected to the inflow lumen 15a of the catheter body 13 and an outflow connector 32 that is connected to the outflow lumen 15b of the proximal catheter body 13. A through lumen port 22 on the hub 17 is connected to the through lumen 15c. The heat exchanger 18 of this catheter embodiment comprises at least first and second coiled heat exchange tube segments 300a, 300b. In some embodiments, additional (e.g., third, fourth) heat exchange tube segments may be used. The heat exchange tube segments 300a, 300b may be formed of any suitable material. In the particular example shown in FIGS. 1 through 3, the heat exchange tube segments 300a, 300b may be advantageously formed of a noncompliant polymeric material, such as polyethylene terephthalate (PET), Pebax, Polyolefin, Polyurethane and/or Nylon, or other suitable compliant or noncompliant material and may be formed of a single tube or one or more tubes. In some embodiments the heat exchange tube segments 30a, 30b may expand and collapse depending on whether or not they are filled with fluid and, in such embodiments, the heat exchange tube segments 30a, 30b may be referred to a "balloons." For some applications, the heat exchange tube segments 30a and 30b may have outer diameters in the range of 2 mm-19 mm and wall thicknesses in the range of 0.0127 mm-0.1 mm.

In one example, the proximal end of the first tube segment 300a is connected to the inflow lumen 15a and the proximal end of the second tube 300b segment is connected to the outflow lumen 15b. The distal ends of the first and second tube segments 300a, 300b are directly or indirectly in fluidic connection with each other such that heat exchanger fluid that has flowed in the distal direction through the first tube segment 300a will then return in the proximal direction through the second tube segment 300b. The distal ends of the heat exchange tube segment 33, 35 are connected to the inflow and outflow connectors 30, 32 of the catheter 12. As seen in detail in FIGS. 6A-6C, the heat exchange assembly 301 may comprise a spine or elongate member 400 and at least one heat exchange member 300 disposed on the spine or elongate member 400. This heat exchange assembly is attached to and extends distally from the proximal body 13, as shown. An introducer sheath may be used to introduce the catheter into a patient's body. Alternatively, the catheter may be introduced without using an introducer sheath.

The term "elongate member" may mean, in at least some embodiments, a member, e.g., a spine or similar structure, which extends from a catheter body and upon which at least one heat exchange member is disposed. In at least some embodiments, the elongate member 400 is distinguishable from the proximal body 13 on the basis of one or more differences in structure or physical property. In the particular embodiment shown, the elongate member 400 comprises an elongate, generally C-shaped member having receiving features 460 which comprise spaced-apart transverse notches, recesses or grooves formed along the open side of the generally C-shaped member. The heat exchange member(s) 300 may be inserted in these recessed, groove, or notch-type receiving features 460 such that the helical loops extend around the closed side of the generally C-shaped elongate member 400. The heat exchange member(s) 300 may be secured to the receiving features 460 by adhesive or other suitable means.

Non-limiting examples of other heat exchange catheters and related apparatus that may be used for some application are described in U.S. Pat. No. 9,492,633, and United States Patent Application Publications Nos. 2013/0090708, 2013/0178923, 2013/0079855, 2013/0079856, 2014/0094880, 2014/0094882, 2014/0094883, and unpublished, copending U.S. patent application Ser. Nos. 15/395,858, 15/395,923 and 15/412,390, the entire disclosure of each such patent and application being expressly incorporated herein by reference. Other examples of catheters that may be used in this invention include those commercially available from ZOLL Circulation, Inc., San Jose, Calif., such as the Cool Line® Catheter, Icy® Catheter, Quattro® Catheter, Solex 7® Catheter, InnerCool® RTx Accutrol Catheter and the InnerCool RTx Standard Catheter. Additionally incorporated herein by reference is the entire disclosure of U.S. patent application Ser. No. 15/594,541, now U.S. Pat. No. 11,116,657, entitled, Devices, Systems and Methods for Endovascular Temperature Control filed on May 12, 2017.

In certain implementations, body temperature control systems and methods wherein the changes in temperature at target locations in a subject's body are estimated or indirectly determined without the need for positioning a temperature sensor at such target location are provided herein.

Figure 7:
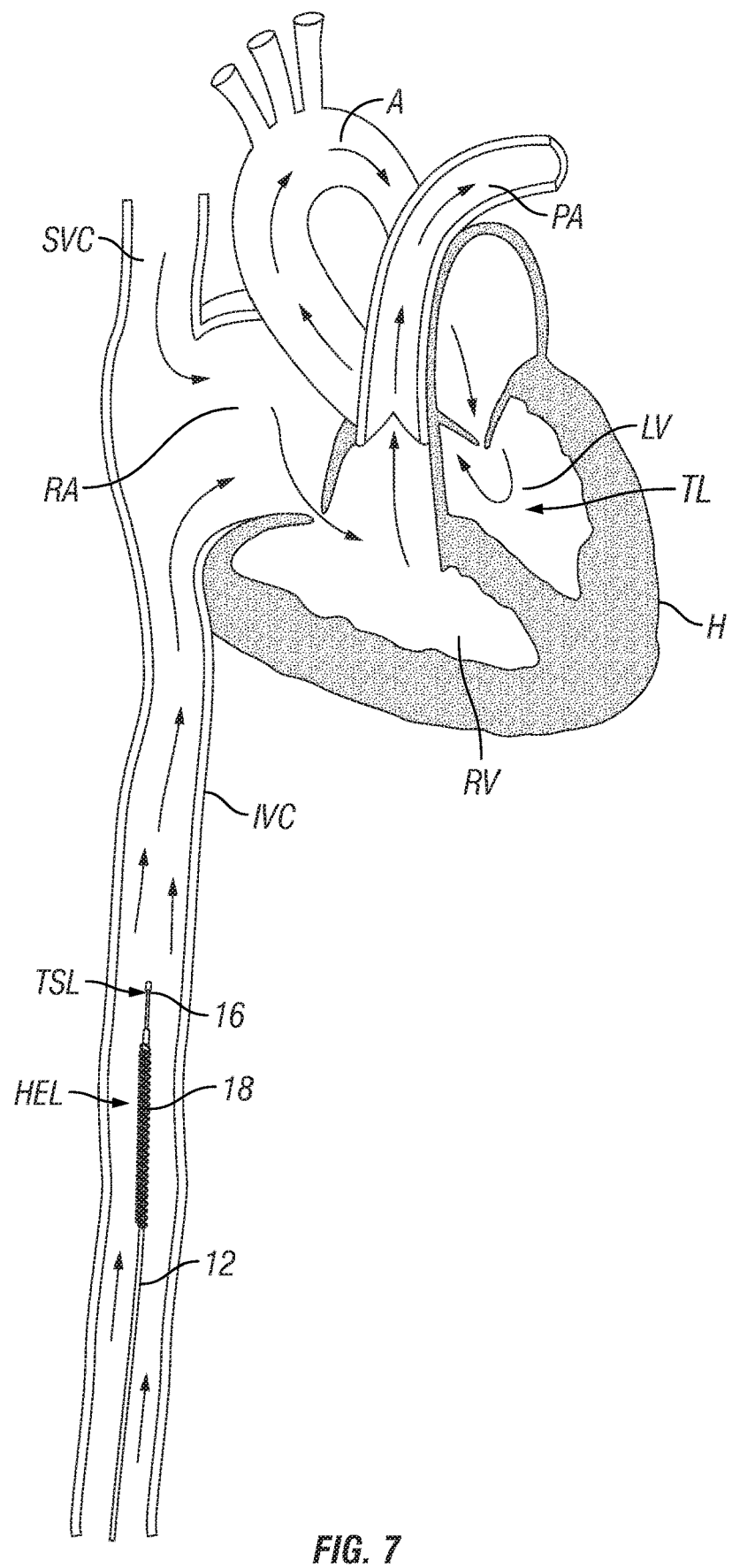
FIG. 7 shows an example of a system/method for controlling a subject's temperature, including left ventricular temperature using an endovascular heat exchange catheter positioned at a heat exchange location in the subject's inferior vena cava and a temperature sensor advanced through the heat exchange catheter and positioned at a temperature sensing location that is also in the subject's inferior vena cava

FIG. 7 shows an example in which a heat exchange system, e.g., the heat exchange system 10 of FIG. 1, is used for controlling a temperature of a patient, e.g., at a Target Location TL within the left ventricle LV of the heart H. In this example, the heat exchange catheter 12 is inserted into a femoral vein FV and advanced until its heat exchanger 18 is at a Heat Exchange Location HEL within the inferior vena cava IVC. The temperature sensor 16 has been advanced through a lumen of the heat exchange catheter 12 to a Temperature Sensing Location TSL within the inferior vena cava IVC downstream of the Heat Exchange Location HEL. In this example, the controller is programmed to use the temperature sensed by the sensor 16 at the Temperature Sensing Location TSL to estimate the temperature at the Target Location TL within the left ventricle LV using the following algorithm:

$$TempLV = TempIVC + (K2-K1) \cdot Power + L$$

wherein:

TempLV is the estimated temperature at the Target Location within the left ventricle;

TempIVC is the current sensed temperature at the temperature sensing location;

K1 is a constant which represents the change in TempLV per Watt of heating or cooling power of the heat exchanger;

K2 is a constant which represents the change in TempIVC per Watt of heating or cooling power; Power is the power output of the heat exchanger; and L is a constant which represents the expected change in the temperature of blood as it circulates through the right heart and lungs. The change in temperature may be due to environmental factors such as the air temperature and humidity level inhaled by the patient, and physiologic factors such as the efficiency and capacity of the patient's lungs. In certain applications and/or under certain conditions L may not be included in the algorithm such that the algorithm would read $TempLV = TempIVC + (K2-K1) \cdot Power$. For example, the expected change in the temperature of blood as it circulates through the right heart and lungs may not be considered and/or may be assumed to have minimal or no effect, e.g. on the LV.

The equation above is derived by considering the principle of Conservation of Energy applied to control volumes within the vasculature of a patient being treated by a heat exchange device (e.g. a temperature management catheter). At least two control volumes within the body are of interest: first, a control volume around the temperature sensor which is immediately downstream of the heat exchange device, second, a control volume around the target organ or tissue of interest. Based on energy conservation, the temperature rise of the control volume, when heat is applied from the heat exchange device, can be described as: Blood temperature rise (delta T)=Power applied by the heat exchange device/(mass flow rate of blood perfusing the control volume*specific heat capacity of blood)*c, where c is an empirically derived constant. A constant K can be defined from the above equation as being equal to c/(mass flow rate of blood*specific heat capacity of blood), and can be computed by measuring the above values, or alternately and preferably by measuring Blood delta T/Power.

The equation for K defined above can then be applied to the control volume of interest. K1 represents the Blood delta T as measured in the target organ or region under the influence of power from a heat exchange catheter placed in the venous system of the body. For example, in the case of AMI, the target organ or region would be the patient's left ventricle, as blood leaving this region flows into the coronary arteries which perfuse the myocardium. K2 represents the blood delta T measured in a patient by a temperature sensor immediately downstream of a heat exchange catheter placed in the venous system of the body. For example, the heat exchange catheter could be placed in the patient's IVC.

In some embodiments, the controller 36 may be programmed with a fixed value for K1 that has been determined based on experimental or historical data. The experimental/historical data may be obtained from subjects who have undergone intravascular cooling and had a left ventricle (LV) temperature probe positioned in their left ventricle to measure LV blood temperature during cooling and during pump stops. The obtained LV values are inserted into the formula below to obtain K1' for each pump stop for each subject. The average of the K1' values is then calculated to provide K1 (as per the formula below), which is used for future subjects to calculate an LV temperature where no LV temperature probe is present. For example, if the rise in LV temperature after a pump stop was 0.75 C, and the power before the pump stop was 500 W, then K1' would be 0.0015. In the animal study cited in paragraphs 92-102 below, a K1 value of 0.002 was used. This number was determined using the method described in this paragraph and the equation below, using data from prior animal studies.

$$k1' = \left( \frac{LV_{At\ X\ sec\ into\ pump\ stop} - LV_{Before\ pump\ stop}}{Power_{Before\ pump\ stop}} \right)$$

$$K1 = \text{average}(K1')$$

The controller 36 may be programmed to calculate K2 at each pump stop using the formula below. For example, if the rise in IVC after a typical pump stop was 3 C, and the power before the pump stop was 500 W, then K2 would be 0.006.

$$k2 = \frac{IVC_{At\ X\ sec\ into\ pump\ stop} - IVC_{Before\ pump\ stop}}{Power_{Before\ pump\ stop}}$$

The value for L, in embodiments where L is utilized, may be stored in the controller as a fixed value equal to the average change in blood temperature between the pulmonary artery PA and left ventricle LV based on experimental or historical data.

The experimental/historical data used to determine L may be obtained from subjects who have undergone intravascular cooling and had a left ventricle (LV) temperature probe positioned in their LV to measure LV blood temperature during cooling and during pump stops, and a pulmonary artery (PA) temperature probe positioned in their PA to measure PA blood temperature during cooling and during pump stops. The obtained actual temperature readings from the left ventricle (ActualTempLV) and pulmonary artery (ActualTempPA) are inserted into the equation ActualTempLV±ActualTempPA=L' to obtain L' for each pump stop for each subject. The average of the L' values is then calculated to provide a L for use by the controller in calculating estimated LV temperature (TempLV) for future subjects in whom a PA temperature probe is present but in whom no LV temperature probe is present, using the formula TempLV=ActualTempPA±L.

To measure Power, the system 10 may be equipped with additional temperature sensors for determining the temperature of heat exchange fluid flowing to the heat exchanger 18 and the temperature of heat exchange fluid flowing from the heat exchanger 18. Such measurements of the heat exchange fluid temperature may be used by the controller 36 to compute the Power output of the heat exchanger 18. Specifically, controller 36 may be programmed to use those measurements of the heat exchange fluid temperature to periodically or continually calculate the value for Power using the following formula:

Power (Watts)=(HE Fluid Temp OUT−HE Fluid Temp IN)·Flow Rate of HE Fluid·CP wherein:
HE Fluid Temp IN is the current measured temperature of heat exchange fluid flowing into the heat exchanger;
HE Fluid Temp OUT is the current measured temperature of heat exchange fluid flowing out of the heat exchanger;
Flow Rate is the measured or calculated volumetric flow rate of heat exchange fluid through the heat exchanger; and
CP is the specific heat capacity of the heat exchange fluid.
E.g., volumetric flow rate may be detected using a flow sensor or in a system that uses a roller pump, volumetric flow rate may be equal to the pump rotational speed multiplied by a constant proportional to the cross sectional area and length of tubing within the pump.
In at least some applications, the heat exchange fluid will be 0.9% NaCl solution, the CP value for which is 4.2 Joules per degree Celsius.

In other embodiments, the controller 36 may be programmed to calculate a K1 at each pump stop using, for example, the following formula:

K1=K2·averageCK ratio wherein averageCK ratio is the ratio of K1 to K2 determined on the basis of experimental or historical data.

The experimental/historical data used to determine averageCK ratio may be obtained from subjects who have undergone intravascular cooling and had a left ventricle (LV) temperature probe positioned in their LV to measure LV blood temperature during cooling and during pump stops, and an inferior vena cava (IVC) temperature probe positioned in their IVC to measure IVC blood temperature during cooling and during pump stops. For each pump stop in the data set, the obtained LV values are inserted into the formula below to obtain K1'.

$$k1' = \left( \frac{LV_{At\ X\ sec\ into\ pump\ stop} - LV_{Before\ pump\ stop}}{Power_{Before\ pump\ stop}} \right)$$

For each pump stop in the data set, the obtained IVC values are inserted into the formula below to obtain K2

$$k2 = \frac{IVC_{At\ X\ sec\ into\ pump\ stop} - IVC_{Before\ pump\ stop}}{Power_{Before\ pump\ stop}}$$

For each pump stop in the data set, K1' and K2 are inserted into the equation CK ratio=K1'/K2 to calculate the CK ratio for each pump stop for each subject. For example, if the K1' was 0.0015 and the K2 was 0.006, then the CKratio would be 0.25. The CK ratios for all pump stops for all subjects are then averaged to provide averageCK ratio for use in calculating K1 using the formula K1=K2·averageCK ratio for future subjects where no LV temperature probe is present.

In other embodiments, $LV_{Before\ pump\ stop}$ can be calculated based on a regression model and a new k1' value can be determined at every pump stop. $LV_{Before\ pump\ stop}$ is known to be dependent on $LV_{At\ X\ sec\ into\ pump\ stop}$ as well as $Power_{Before\ pump\ stop}$. Therefore, a regression analysis can be used to develop a relationship using existing preclinical data.

Based on multiple linear regression, the following relationship may be obtained:

$$LV_{Before\ pump\ stop}=a0+(a1*LV_{At\ X\ sec\ into\ pump\ stop})+(a2*Power_{Before\ pump\ stop})$$

Where a0=−2.4691, a1=1.0674, a2=−0.03. Based on this equation a new k1' value can be determined at every pump stop following the equation $$k1' = \left( \frac{LV_{At\ X\ sec\ into\ pump\ stop} - LV_{Before\ pump\ stop}}{Power_{Before\ pump\ stop}} \right)$$

This can then in turn be used in the above equation to calculate the estimated temperature at the Target Location within the left ventricle.

In some embodiments where the pump 34 is stopped periodically or occasionally and K1 is a fixed value based on experimental or historical data (as discussed herein), the controller may be programmed to apply the above-described algorithms for ongoing recalculation of K2 by a process that comprises the following steps:
calculating and recording Power before a pump stop;
recording the temperature at the Temperature Sensing Location (e.g., the IVC temperature) before pump stop;
effecting pump stop;
recording the temperature at the Temperature Sensing Location (e.g., the IVC temperature) at x seconds into said pump stop;
calculating a new K2 value if the Power recorded before said pump stop is greater than a predetermined threshold value; and
applying the new K2 value, if calculated, for subsequent LV calculation.

As shown above, calculation of K2 requires computation of a quotient containing the factor "Power before pump stop" in the denominator. If this factor is exactly equal to zero, and the numerator is non-zero, the calculated K2 becomes infinite. Having an infinite K2 causes the calculation for TempLV to become infinite for non-zero power levels, which is not useful. In principle, if the denominator of the K2 equation (Power before a pump stop) becomes zero, the numerator (IVC x sec into pump stop−IVC before pump stop) would also be expected to become zero. That is, if there is no measured power, there should be no change in IVC temperature. This would result in a calculation of 0/0, which is mathematically indeterminate, and is not a usable result as calculation of TempLV could not be completed. Similarly, if the numerator and denominator of the K2 calculation are both near zero, the results are finite but highly uncertain, as small measurement errors will have a large effect on the resulting K2. For example, if the rise in IVC after a typical pump stop was 3 C, and the power before the pump stop was 500 W (K2 would be 0.006), and the power measurement was in error by +10 Watts, K2 would have an error of +2% which is acceptable. However if IVC temperature rise and power were very small, (for example, 0.12 C, and 20 W) and the same error was present (+10 W), the calculation would be in error by 100%. Whereas in the previous situations computation could not be completed, this scenario presents more risk to the patient as a sensible K2 is computed but is in fact erroneous and will lead to unacceptable estimates for TempLV. To avoid this scenario, the algorithm should avoid calculating K2 when catheter power before a pump stop is below a predetermined threshold. The value of this threshold depends on the accuracy of the IVC temperature reading, and the accuracy of the catheter power calculation. The power calculation is in turn dependent on the accuracy of the catheter inlet and outlet temperature measurements, and the accuracy of the catheter flow rate measurement. In practice this threshold is in the range of 10 to 60 Watts, e.g., 30 Watts.

In some embodiments where the pump 17 is stopped periodically or occasionally and both K1 and K2 are recalculated at each pump stop, the controller 36 may be programmed to apply the above-described algorithms for ongoing recalculation of K1 and K2 by a process that comprises the following steps:

calculating and recording Power before a pump stop;
recording temperature at the Temperature Sensing Location (e.g., the IVC temperature) before said pump stop;
effecting the pump stop;
recording temperature at the Temperature Sensing Location (e.g., the IVC temperature) at x seconds into said pump stop;
if the Power recorded before said pump stop is greater than a predetermined threshold value, calculating new K1 and K2 values, and
applying the new K1 and K2 values, if calculated, for subsequent LV calculation.

In some embodiments, the calculation of K1 and/or K2 may be based on running average, median or filtered value. In such embodiments, the controller 36 may, for example, be programmed to apply the above-described algorithms by a process that comprises the following steps:

calculating and recording Power before a pump stop;
recording temperature at the Temperature Sensing Location (e.g., the IVC temperature) before the pump stop;
effecting said pump stop;
recording temperature at the Temperature Sensing Location (e.g., the IVC temperature) at x seconds into said pump stop;
if the Power recorded before said pump stop is greater than a predetermined threshold value, calculating a new K2 value; and
if a new K2 value has been calculated, calculating a running average, median or filtered K2 value based on the new K2 value and one or more previous K2 values and, thereafter, using said running average, median or filtered K2 value for LV calculation.

Figures 8, 9:
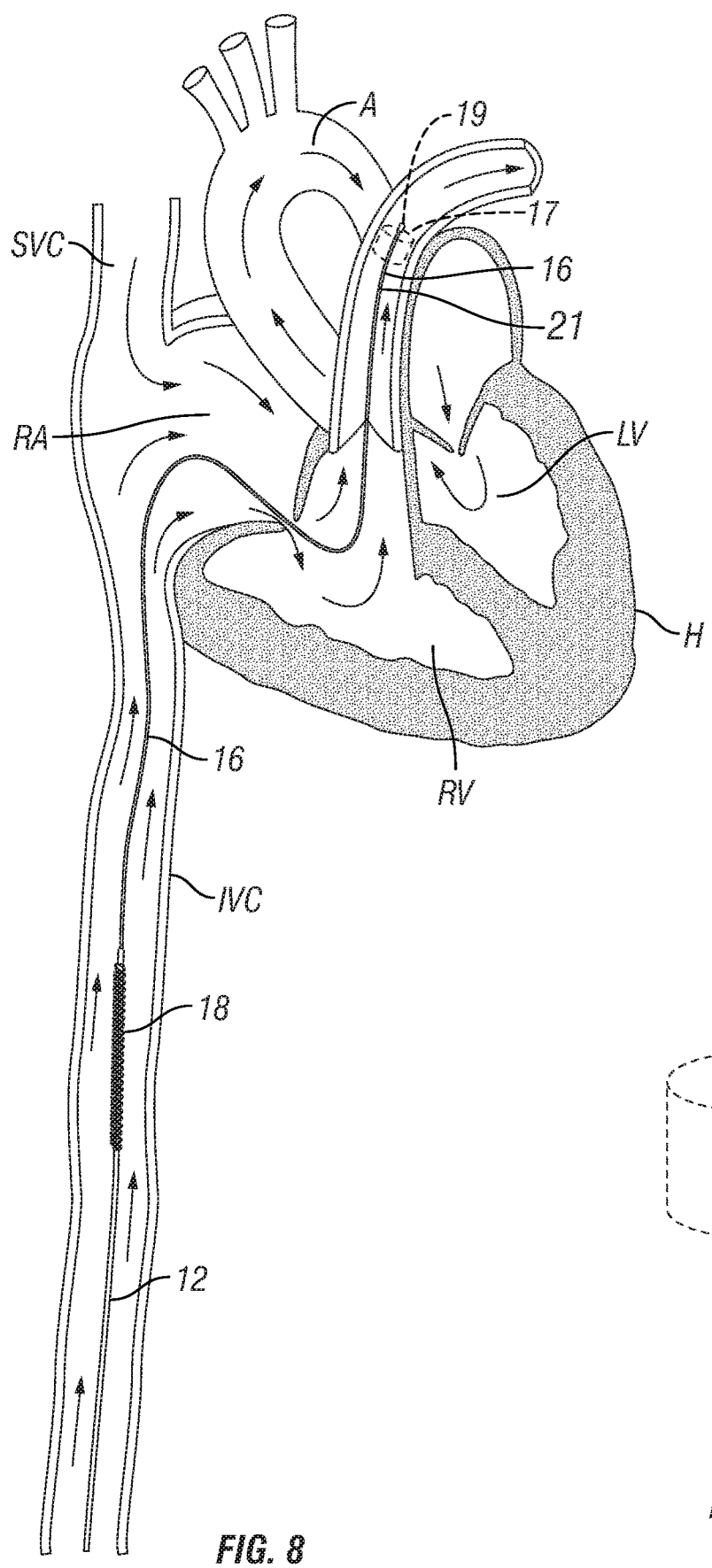
FIG. 8 shows an example of a system/method for controlling a subject's temperature, including left ventricular temperature using an endovascular heat exchange catheter positioned at a heat exchange location in the subject's inferior vena cava and a temperature sensor advanced through the heat exchange catheter and positioned at a temperature sensing location in the subject's pulmonary artery.
FIG. 9 is an enlarged view of the distal portion of the temperature sensor shown in FIG. 8.

FIG. 8 shows another example of a system/method for controlling temperature at a Target Location TL in the left ventricle LV using an endovascular heat exchange catheter 12 positioned at a Heat Exchange Location HEL in the subject's inferior vena cava IVC (e.g., via femoral access) and a temperature sensor 16 positioned at a Temperature Sensing Location in the subject's pulmonary artery PA. In this particular example, the temperature sensor 16 has been advanced through the heat exchange catheter 12 and into the pulmonary artery PA. However, temperature sensors may be placed in the pulmonary artery PA by numerous other means, some examples of which are discussed below. In some embodiments, the temperature sensor in the PA may be placed via insertion through the internal jugular (IJ) or subclavian vein (SV).

The temperature of mixed venous blood flowing through the pulmonary artery PA is typically within about 0.5 degrees C. of the temperature in the left ventricle, e.g., between 0.02 and 0.07 degrees C. This is based on pig experiments where a temperature probe was placed in the right ventricle of a pig, immediately upstream of the pulmonary artery, and a second temperature probe was placed in the left ventricle. The difference between the temperature in the pulmonary artery PA and that in the Left Ventricle LV is due to the gain or loss of heat as the blood circulates through the lungs, i.e., the above defined "lung constant" (L). In some applications where a coarse approximation of left ventricular temperature is acceptable, the measured temperature in the pulmonary artery PA may be used, either without modification or after subtraction of a predetermined correction factor or L intended to account approximately for the lung effect (e.g., −0.1° C., −0.2° C., −0.3° C., −0.5° C., etc.), as a surrogate for the left ventricular temperature. In other applications, the controller 36 may be programmed to calculate the estimated left ventricular temperature using the following formula:

$$TempLV = PA \pm L$$

wherein:
TempLV means estimated left ventricular temperature;
PA means sensed pulmonary artery temperature; and
L is a constant which represents the expected change in temperature of blood as it circulates through the right heart and lungs, which may be determined or estimated as described above.

With particular reference to FIG. 9, the temperature sensor 16 may comprise an elongate, flexible shaft such as a wire or catheter having one or more temperature measuring devices (e.g., thermistor(s)) thereon or therein to measure temperature at the desired Temperature Sensing Location. Optionally, to facilitate flow-directed advancement of the temperature sensor 16 into the pulmonary artery PA, an inflatable balloon or other buoyant member 17 may also be provided on the elongate shaft. Flow-directed placement of a pulmonary artery catheter using a balloon is a technique well known in the art. Also, optionally, one or more additional port(s) and/or port(s) and/or sensor(s) 17 may be positioned on the elongate shaft for monitoring additional variables or parameters within the pulmonary artery (e.g., pulmonary artery pressure, pulmonary artery wedge pressure, pulmonary artery flow rate, continuous cardiac output, etc.).

Figure 10:
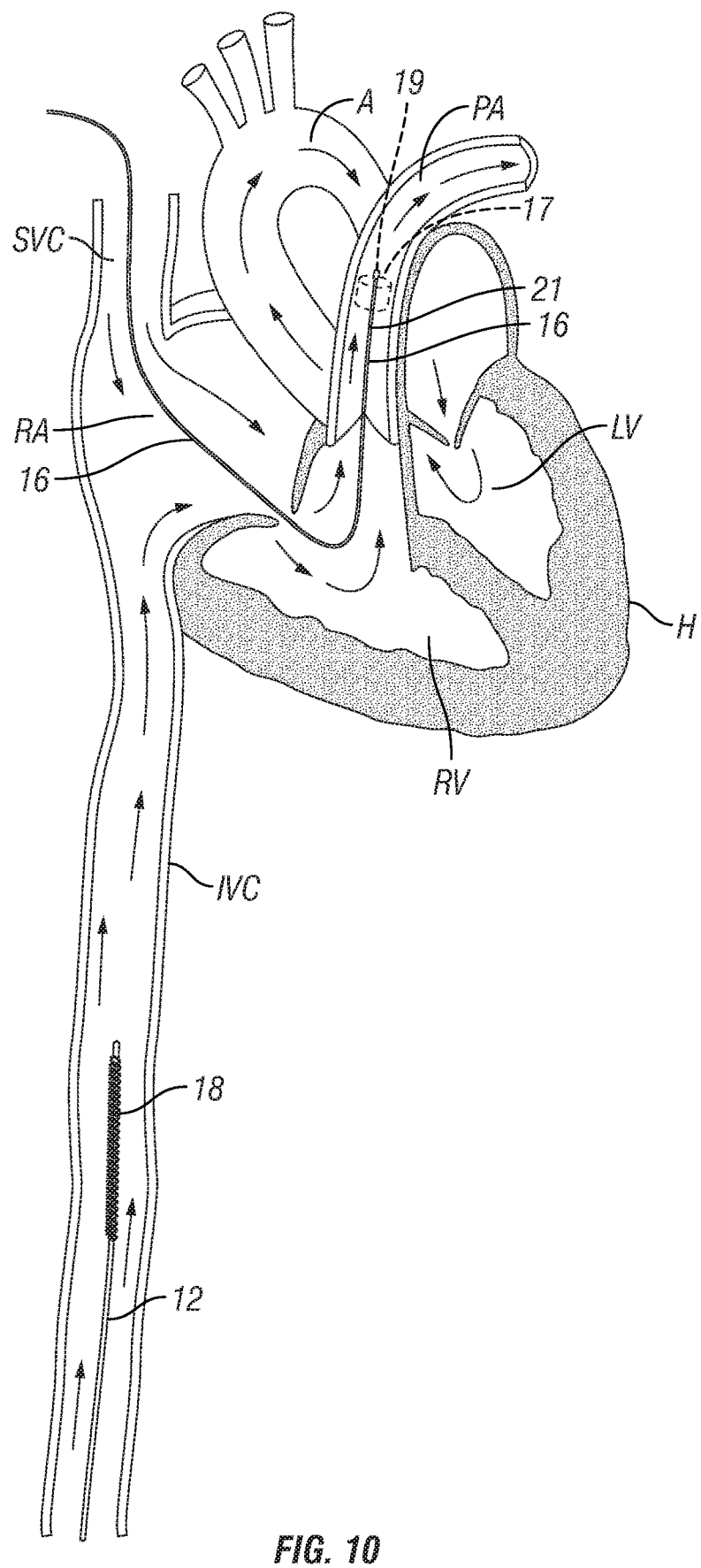
FIG. 10 shows an example of a system/method for controlling a subject's temperature, including left ventricular temperature using an endovascular heat exchange catheter positioned at a heat exchange location in the subject's inferior vena cava and a temperature sensor that has been advanced via the superior vena cava to a temperature sensing location in the subject's pulmonary artery.

FIG. 10 shows another non-limiting example in which the heat exchange catheter 12 is advanced into the subject's inferior vena cava IVC and its heat exchanger 18 is positioned at a Heat Exchange Location HEL in the inferior vena cava IVC and a separate temperature sensor 16 is advanced to a Temperature Sensing Location in the pulmonary artery PA. In this manner, the temperature at the Target Location TL in the left ventricle LV may be determined in the same manner as described above in relation to FIG. 3, but in this approach the temperature sensor 16 is not advanced through the heat exchange catheter 12. As described above, the temperature sensor 16 shown in FIG. 5 may optionally be equipped with a balloon 17 and/or port(s) and/or sensor(s)

17 for monitoring additional variables or parameters within the pulmonary artery PA. In some cases, the pulmonary temperature sensor 16 may be incorporated in a pulmonary artery catheter, such as a Swan-Gantz catheter, having other functions for hemodynamic monitoring in addition to the temperature sensor.

Figure 11:
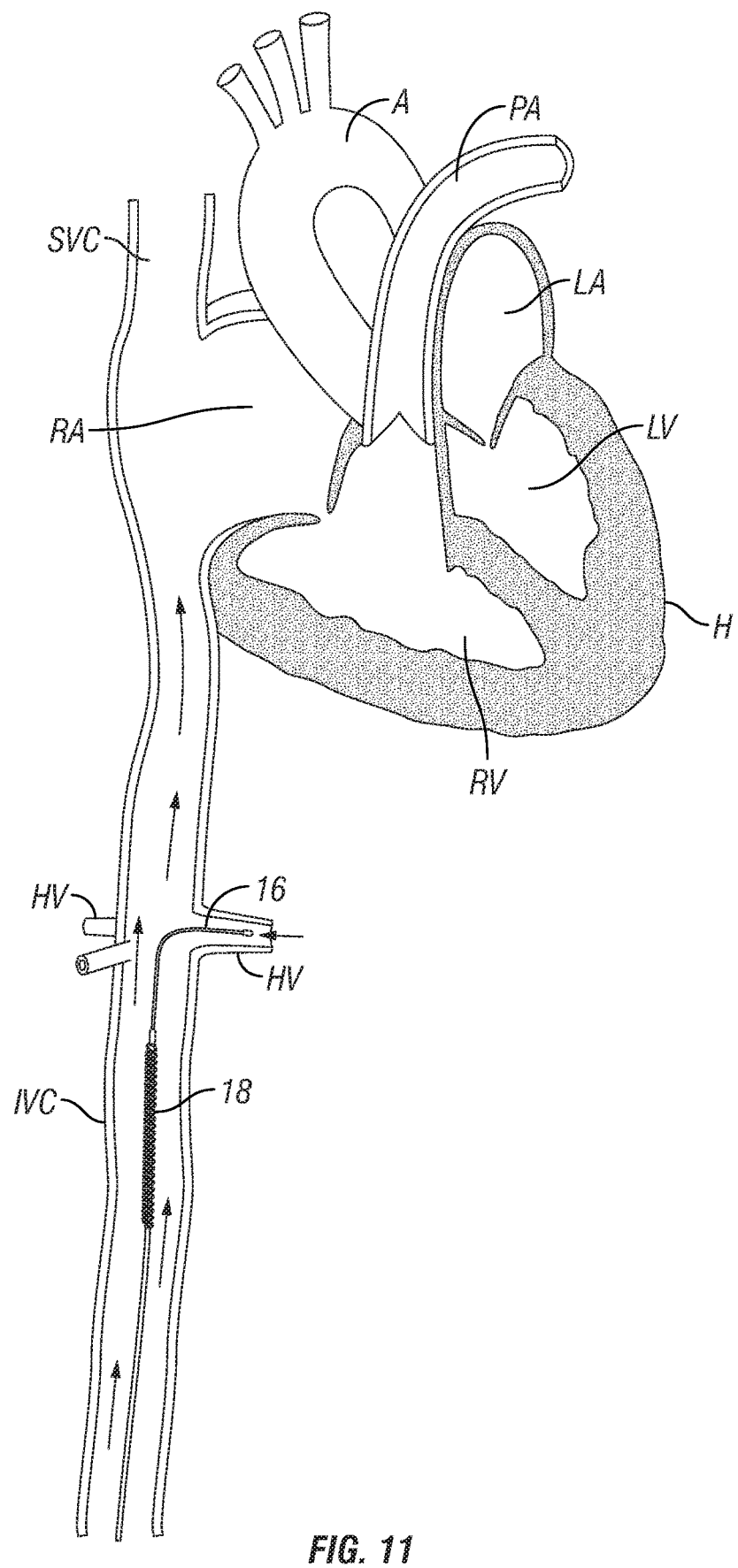
FIG. 11 shows an example of a system/method for controlling a subject's temperature, including left ventricular temperature using an endovascular heat exchange catheter positioned at a heat exchange location in the subject's inferior vena cava and a temperature sensor advanced through the heat exchange catheter and positioned at a temperature sensing location in a hepatic vein of the subject.

In the example of FIG. 11, the heat exchange catheter 12 is advanced into the subject's inferior vena cava IVC and its heat exchanger 18 is positioned at a Heat Exchange Location HEL in the inferior vena cava IVC. The temperature sensor is advanced through a lumen of the heat exchange catheter and to a Temperature Sensing Location within a hepatic vein HV. In this embodiment, the controller 36 may be programmed to calculate estimated temperature at the Target Location in the left ventricle LV using the following formula:

$$TempLV = HV \pm K_{hepatic}$$

wherein:
TempLV means estimated left ventricular temperature;
HV means sensed hepatic vein temperature; and
$K_{hepatic}$ is a constant which represents the expected change in temperature of blood as it circulates through the subject's liver In the embodiment of FIG. 11, the controller 36 may be pre-programmed with a value for $K_{hepatic}$ based on previous experimental or historical data. The experimental/historical data used to determine $K_{hepatic}$ may be obtained from subjects who have undergone intravascular cooling and had a left ventricle (LV) temperature probe positioned in their actual left ventricle (ActualTempLV) to measure left ventricular blood temperature during cooling and during pump stops, and a hepatic vein (HV) temperature probe positioned in their HV to measure HV blood temperature during cooling and during pump stops. The obtained ActualTempLV values and HV values are inserted into the equation ActualTempLV±HV=K'$_{hepatic}$, to obtain K'$_{hepatic}$ for each pump stop for each subject. The average of the K'$_{hepatic}$ values is then calculated to provide $K_{hepatic}$ for use by the controller in calculating estimated left ventricular temperature (TemoLV) in future subjects where no LV temperature probe is present, using the formula TempLV=HV±$K_{hepatic}$.

Figure 12:
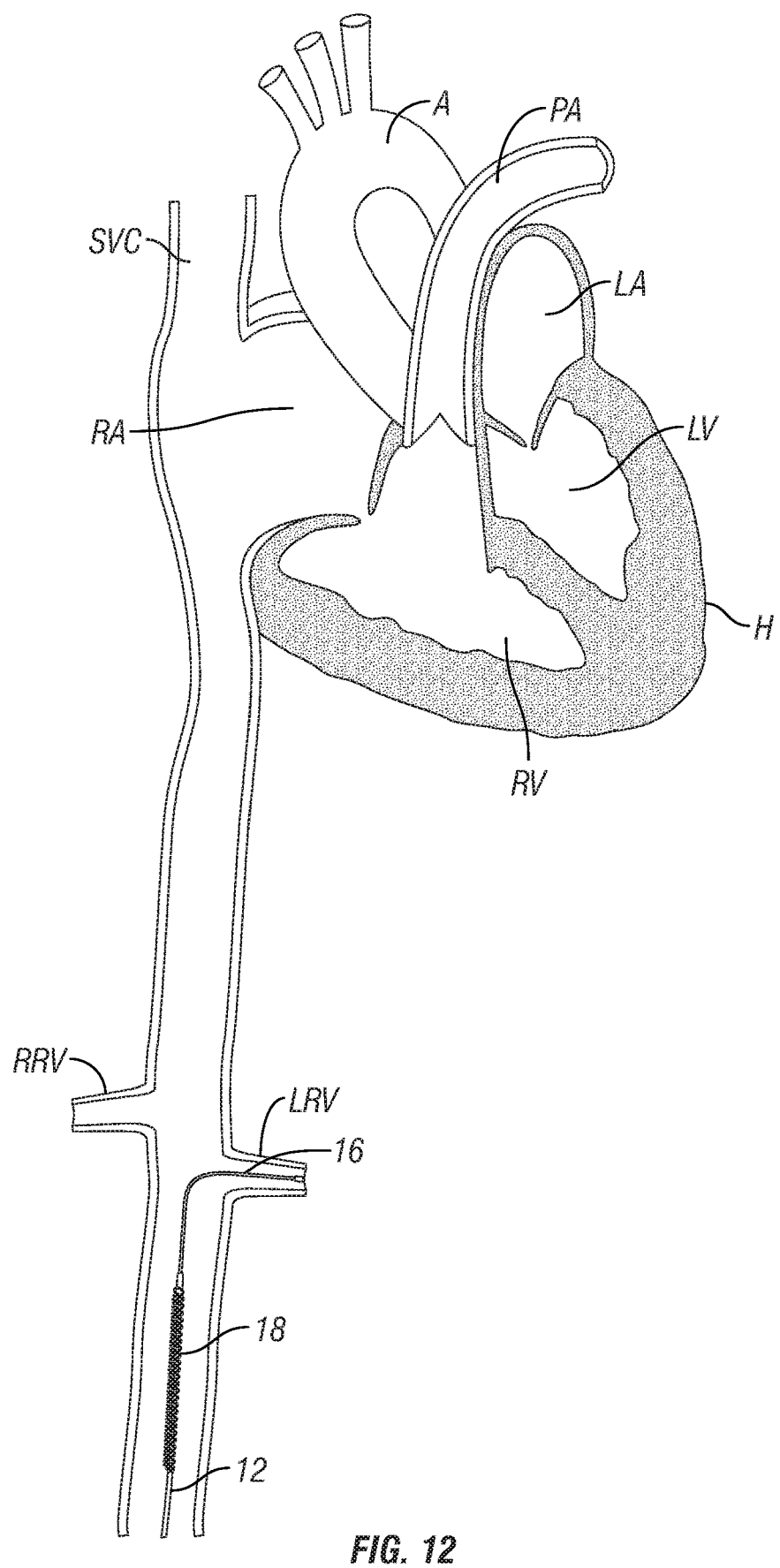
FIG. 12 shows an example of a system/method for controlling a subject's temperature, including left ventricular temperature using an endovascular heat exchange catheter positioned at a heat exchange location in the subject's inferior vena cava and a temperature sensor advanced through the heat exchange catheter and positioned at a temperature sensing location in a renal vein of the subject.

FIG. 12 shows an example that is similar to the approach used in FIG. 11, but wherein the temperature sensor 16 is advanced to a Temperature Sensing Location within the left renal vein LRV. The right renal vein RRV may be used as an alternative. In this example, the controller 36 may be programmed to calculate estimated temperature at the Target Location in the left ventricle LV using the following formula:

$$TempLV = RV \pm K_{kidney}$$

wherein:
TempLV means estimated left ventricular temperature;
RV means sensed renal vein temperature; and
$K_{kidney}$ is a constant which represents the expected change in temperature of blood as it circulates through the subject's kidney.

In the embodiment of FIG. 11, the controller 36 may be pre-programmed with a value for $K_{Kidney}$ based on previous experimental or historical data. The experimental/historical data used to determine $K_{kidney}$ may be obtained from subjects who have undergone intravascular cooling and had a left ventricle (LV) temperature probe positioned in their LV to measure the actual left ventricular blood temperature (ActualTempLV) during cooling and during pump stops, and a renal vein (RV) temperature probe positioned in their RV to measure RV blood temperature during cooling and during pump stops. The obtained ActualTempLV values and RV values are inserted into the equation ActualTempLV±RV=K'$_{kidney}$ to obtain K'$_{kidney}$ for each pump stop for each subject. The K'$_{kidney}$ for all subjects are then averaged to provide a $K_{kidney}$ for use by the controller in calculating estimated LV temperature (TempLV) for future subjects where no LV temperature probe is present, using the formula TempLV=RV±$K_{kidney}$.

Figure 13:
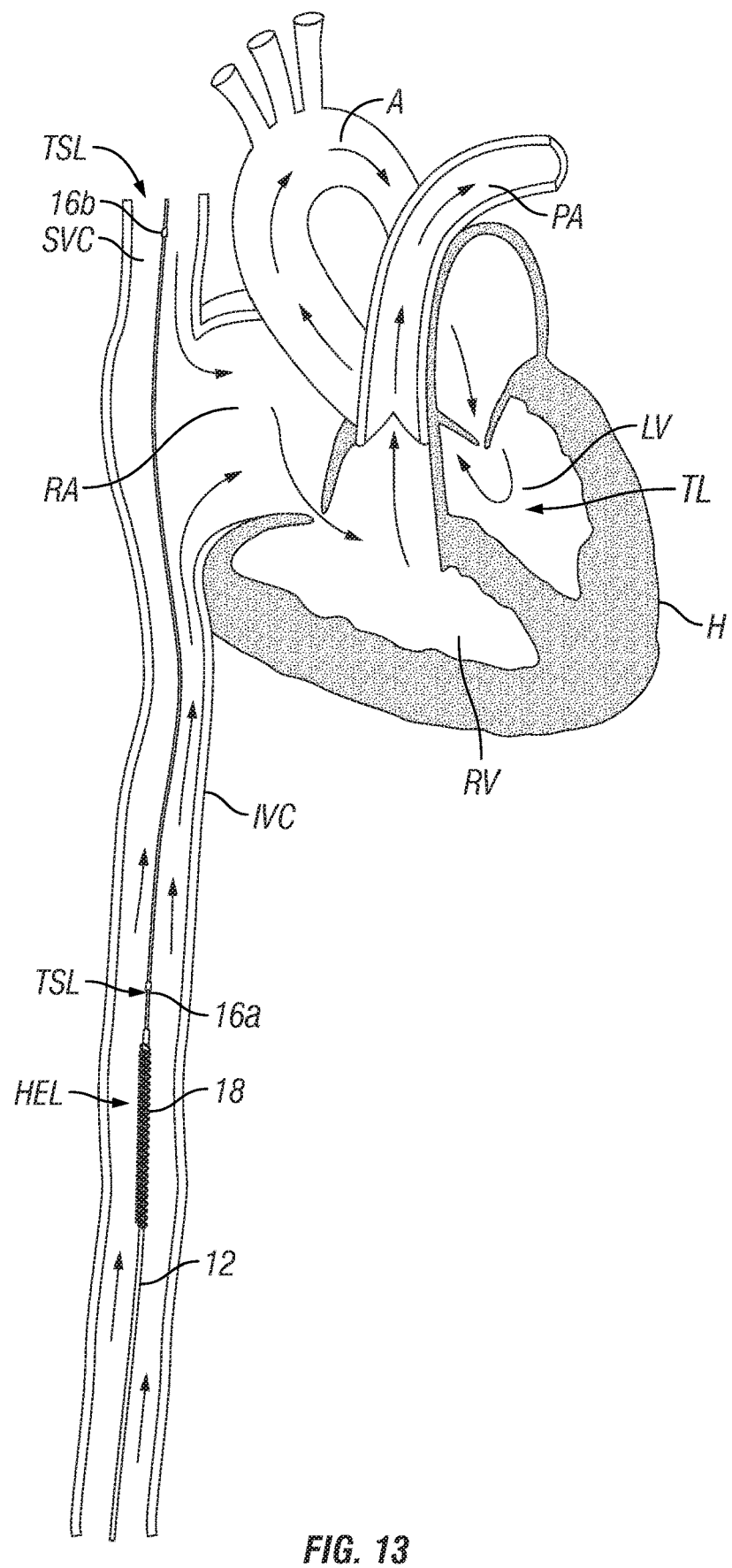
FIG. 13 shows an example of a system/method for controlling a subject's temperature, including left ventricular temperature using an endovascular heat exchange catheter positioned at a heat exchange location in the subject's inferior vena cava and a temperature sensors positioned at temperature sensing locations in the inferior vena cava and superior vena cava.

FIG. 13 shows an example in which two temperature sensors 16a, 16b are used. In this example, the endovascular heat exchange catheter 12 is advanced into the inferior vena cava (e.g., via femoral access) such that its heat exchanger 18 is positioned at a Heat Exchange Location HEL in the subject's inferior vena cava IVC. An elongate temperature probe comprising the temperature sensors 16a, 16b is advanced through the heat exchange catheter and to a position where the first temperature sensor 16a is at a Temperature Sensing Location in the inferior vena cava and the second temperature sensor 16b is at a Temperature Sensing Location in the superior vena cava SVC. In alternative embodiments, the temperature sensor in the SVC may be placed via insertion through the internal jugular (IJ) or subclavian vein (SV). In this example, the controller 36 may be programmed to calculate the estimated temperature at a Target Location in the left ventricle LV (TempLV) using the following formula:

$$TempLV = (SVC \cdot 1/r+1) + (IVC \cdot r/r+1) \pm L$$

wherein:
TempLV means estimated left ventricular temperature;
SVC means sensed superior vena cava temperature;
IVC means sensed inferior vena cava temperature;
r means ratio of SVC flow rate to IVC flow rate; and
L is a constant which represents the expected change in the temperature of blood as it circulates through the right heart and lungs, which may be determined in the manner discussed above.

The controller 36 may be pre-programmed with a value for r based on previous experimental or historical data. The experimental/historical data used to determine r may be obtained from subjects who have undergone intravascular cooling and had a left ventricle (LV) temperature probe positioned in their LV to measure actual LV blood temperature (ActualTempLV) during cooling and during pump stops, and a SVC flow sensor positioned in their SVC to measure SVC blood flow rate during cooling and during pump stops and an IVC flow sensor positioned in their IVC to measure IVC blood flow rate during cooling and during pump stops. The SVC blood flow rate and the IVC blood flow rate for all subjects are then averaged and the ratio of the average SVC blood flow rate and average IVC blood flow rate=r, which is used by the controller in calculating estimated LV temperature (TempLV) for future subjects where no LV temperature probe is present, using the formula TempLV=(SVC·1/r+1)+(IVC·r/r+1)±L.

In other embodiments, the heat exchange catheter may be advanced into the subject's inferior vena cava IVC (e.g., via femoral access) and its heat exchanger is positioned at a Heat Exchange Location HEL in the inferior vena cava IVC. A temperature sensor may positioned in a Temperature Sensing Location within one or more of the right or left internal jugular veins (IJ), the right or left subclavian veins, the right or left innominate veins or the superior vena cave (SVC). Temperature offsets may be determined for each of these locations: the upper body (SVC or innominate vein); the arm (subclavian); the head (internal jugular) In certain embodiments, the controller may be programmed to calculate estimated temperature at the Target Location in the left ventricle LV using the following formulas:

$$TempLV = SVC \text{ or } Innominate \pm K_{upper\ body}$$

$$TempLV = subclavian \pm K_{subclavian}$$

$$TempLV = jugular \pm K_{jugular}$$

wherein:

TempLV means estimated left ventricular temperature;

SVC or Innominate means sensed SVC or Innominate vein temperature; Subclavian means sensed subclavian vein temperature; jugular means sensed internal jugular vein temperature; and $K_{upper\ body}$ is a constant which represents the expected change in temperature of blood as it circulates through the subject's upper body (SVC or innominate vein), $K_{subclavian}$ is a constant which represents the expected change in temperature of blood as it circulates through the subject's subclavian vein, $K_{jugular}$ is a constant which represents the expected change in temperature of blood as it circulates through the subject's internal jugular vein.

A controller may be pre-programmed with a value for $K_{upper\ body}$, $K_{subclavian}$, or $K_{jugular}$ based on previous experimental or historical data. The experimental/historical data used to determine these values may be obtained from subjects who have undergone intravascular cooling and had a left ventricle (LV) temperature probe positioned in their LV to measure actual LV blood temperature (ActualTempLV) during cooling and during pump stops, and an SVC, innominate, subclavian, or internal jugular temperature probe positioned in their SVC, innominate, subclavian, or internal jugular to measure SVC, innominate, subclavian, or internal jugular blood temperature during cooling and during pump stops. For example, the obtained ActualTempLV values and SVC values are inserted into the equation ActualTempLV±SVC=K'$_{upper\ body}$ to obtain K'$_{upper\ body}$ for each subject. The K'$_{upper\ body}$ for all pump stops for all subjects are then averaged to provide a $K_{upper\ body}$ for use by the controller in calculating estimated left ventricular temperature (TempLV) temperature for future subjects where no LV temperature probe is present, using the formula TempLV=SVC±$K_{upper\ body}$. These steps can be performed for the innominate, subclavian or internal jugular values as well, using their respective equations (above).

In certain embodiments, the duration of a pump stop may be reduced by draining or reducing the capacitance in the tubing (e.g., in the inflow line connecting the console (e.g., via a cassette within the console) to the catheter) through which the heat exchange fluid flows, more quickly. As a result, it would take less time for the heat exchange fluid flow to stop after a pump stop, thereby reducing the temperature decay time of the catheter. This may be accomplished by running the pump backwards until the cassette pressure sensor reads>5 psi. For example, using this method, it would take about 7 seconds for heat exchange fluid flowing at a rate of about 410 ml/min to stop flowing.

Other implementations of body temperature control systems and methods wherein the changes in temperature at target locations in a subject's body are estimated or indirectly determined without the need for positioning a temperature sensor at such target location are described herein.

In another embodiment, a system for warming or cooling a target organ or anatomical region within a subject's vasculature to a target temperature may include a heat exchanger. The heat exchanger may be configured to exchange heat with the subject's flowing blood at a heat exchange location. The system may include a first temperature sensor, which sensor can sense the temperature of the subject's flowing blood at a temperature sensing location. The first temperature sensor may be positioned downstream from the heat exchanger relative to a direction of the flowing blood. The system also includes a controller. The controller may receive signals from the temperature sensor indicative of the blood temperature being sensed at the temperature sensing location. The controller includes a processor programmed to estimate the temperature at the target organ or anatomical region. The temperature is estimated based on the following: the temperature sensed at the temperature sensing location; a heat capacity of at least one intervening organ or anatomical region between the temperature sensing location and the target organ or anatomical region; and a power output of the heat exchanger. Relative to the direction of the flowing blood, the intervening organ or anatomical region is located downstream from the first temperature sensor, and the target organ or anatomical region is located downstream from the intervening organ or anatomical region. Based on the estimated temperature at the target organ or anatomical region, the controller can control the heat exchanger to warm or cool blood flowing through the heat exchange location as needed to result in warming or cooling of the target organ or anatomical region to the target temperature.

In certain embodiments, the heat capacity of at least one intervening organ or anatomical region between the temperature sensing location and the target organ or anatomical region may be predetermined and/or estimated.

For example, the processor may be programmed to estimate the temperature at the target organ or anatomical region based on the heat capacities of at least two intervening organs or anatomical regions between the temperature sensing location and the target location. The heat capacity of a first intervening organ or anatomical region is predetermined, while the heat capacity of a second intervening organ or anatomical region is estimated.

In other embodiments, the heat capacity of at least one intervening organ or anatomical region between the temperature sensing location and the target organ or anatomical region may be represented by a predetermined constant based on historical experimental temperature data of the intervening organ or anatomical region.

The system may include a pump for pumping a heat exchange fluid through the heat exchanger to exchange heat with the subject's flowing blood. The pumping of said heat exchange fluid through the heat exchanger may be stopped periodically or occasionally and the heat capacity of at least one intervening organ or anatomical region between the temperature sensing location and the target organ or anatomical region may be estimated or otherwise calculated at each pump stop.

In certain embodiments, where the temperature of the left ventricle is estimated and the heat exchanger is positioned in the inferior vena cava, at least one intervening organ or anatomical region between the temperature sensing location and the target organ or anatomical region may include at least a portion of the inferior vena cava and the left ventricle.

In certain embodiments, the system may include a first and second temperature sensor. The first temperature sensor may be located distal to the heat exchanger and the second temperature sensor may be located proximal to the heat exchanger. The heat capacity of at least one intervening organ or anatomical region between the temperature sensing location and the target organ or anatomical region may be estimated without a pump stop or with a pump stop having a reduced duration by calculating the difference between the temperature sensed by the first sensor and the temperature sensed by the second sensor, and utilizing that difference in the estimation or calculation of the heat capacity of at least one intervening organ or anatomical region between the temperature sensing location and the target organ or anatomical region. In certain embodiments, the first and second temperature sensors may be located is the inferior vena cava, or in any other region of the body, depending on the location of the target organ or anatomical region. For example, the target organ or anatomical region may include the left ventricle, brain, kidney or liver.

In certain embodiments, the system may include first temperature sensor located distal to a heat exchanger. The first temperature sensor may be posited in the inferior vena cave and a second temperature sensor may be positioned in the esophagus, such that the heat capacity of an organ or anatomical region near the esophagus can be estimated.

In certain embodiments, the system may include first temperature sensor located distal to a heat exchanger. The first temperature sensor may be posited in the inferior vena cave and a second temperature sensor may be positioned in the pulmonary artery, such that the heat capacity of an organ or anatomical region near the pulmonary artery can be estimated.

In other embodiments, the heat capacity of at least one intervening organ or anatomical region between the temperature sensing location and the target organ or anatomical region may be estimated and/or adjusted based on one or more patient parameters, e.g., weight, girth, and muscle mass.

In certain embodiments, any of the above describes systems may be utilized where the target organ or anatomical region is within the left ventricle of the subject's heart, the heat exchange location is within the subject's inferior vena cava or superior vena cava, and the temperature sensing location is in the subject's vasculature downstream of the heat exchange location. Optionally, both the heat exchange location and the temperature sensing location may be in the subject's inferior vena cava. The system controller may adjust the power of the heat exchanger based on an estimated temperature at the target organ or anatomical region.

In one example, a system may include a controller programmed to estimate temperature at the target location within the left ventricle (TempLV) using the algorithm:

$$TempLV=IVC+Power(K2-K1+K_{LUNG}):$$

TempLV=is the estimated temperature at the target location within the left ventricle;

IVC=is the current sensed temperature at the temperature sensing location;

K1=is a constant which represents the change in LV Temperature per Watt of eating or cooling power of the heat exchanger;

K2=is a constant which represents the change in IVC temperature per Watt of heating or cooling power;

Power=is the power output of the heat exchanger; and $K_{LUNG}$=is a constant which represents the change in the temperature of blood as it circulates through the right heart and lungs per Watt of heating or cooling power of the heat exchanger In certain embodiments, K1, K2, and Klung are inversely proportional to specific heat capacity, where the units of K1, K2 and Klung are in degrees Celsius/Watt, which is the inverse of the standard definition of heat capacity, which is J/degrees Celsius. Furthermore, as mentioned above, K1 K2 may be defined as being equal to c/(mass flow rate of blood*specific heat capacity of blood). K1, K2 and Klung may also be thought of as representing a form of heat responsiveness, or alternately heat capacity, in the sense that they represent the organ's or anatomical region's responsiveness to heat.

Estimation of Left Ventricular Temperature in Anesthetized Swine

Applicant has confirmed the accuracy and feasibility of one embodiment of the present invention in animals. Eight (8) adult swine having body weights ranging from 42 kg to 101 kg were anesthetized with isoflurane, intubated and placed on mechanical ventilation. Data from one animal was excluded from this analysis due to hardware issues encountered during testing. In each animal, a Triton™ endovascular heat exchange catheter (ZOLL Circulation, Inc., San Jose, Calif.) was inserted into the femoral vein and advanced to a position within the inferior vena cava. Specifics of the Triton™ endovascular heat exchange catheter are described in U.S. patent application Ser. No. 15/395,858 entitled Fluid-Circulating Catheters Useable for Endovascular Heat Exchange, the entire disclosure of which is expressly incorporated herein by reference. Also, the heat exchange catheter used in this example is shown in FIGS. 5 through 6C of this patent application and summarized above. A Triton endovascular temperature probe ("IVC Probe") was inserted through the working lumen of the heat exchange catheter and advanced to a position within the inferior vena cava approximately 2 cm downstream of the heat exchange catheter's heat exchanger. A temperature probe ("LV Control Probe") was also placed in the left ventricle to directly monitor the actual temperature within the left ventricle. Three (3) additional probes ("Extracardiac Control Probes") were also placed in each animal, within the SVC, aorta, and contralateral iliac vein to document the occurrence of any temperature related adverse events. All temperature probes were connected to the AD instruments Power lab 16/30 DAQ system and the data was recorded. The heat exchange catheter and the IVC Temperature Probe were also connected to a Thermogard XP3 System Console (ZOLL Circulation, Inc., San Jose, Calif.), particulars of which are described in U.S. patent application Ser. No. 15/423,581 entitled Devices, Systems and Methods for Endovascular Temperature Control, the entire disclosure of which is expressly incorporated herein by reference. Also, the system console and related disposables used in this example are shown in FIGS. 1 through 4 of this patent application and summarized above.

In this experiment, the Temperature Sensing Location L is the inferior vena cava (IVC Probe) and the Target Location TL is the left ventricle LV, as generally shown in FIG. 1. The controller of a system described herein, e.g., the Thermogard XP3 System Console, is programmed to cause the Console's pump to perform pump stops and to use the temperature sensed by the IVC Probe as the Temperature Sensing Location TSL and to estimate the temperature at the Target Location TL within the left ventricle LV using the algorithm (TempLV=TempIVC+(K2−K1)·Power) and procedure described above. Alternatively, TempLV=TempIVC+(K2−K1)·Power+L could be used. Pump stops occurred as follows:

| Pump Stop Number | Timing of Pump Stop |
| --- | --- |
| 1 | 90 seconds after commencement of cooling |
| 2 | When the estimated LV temperature has been lowered to 1.5 degrees C. above the target temperature (i.e., at 33.5 degrees C.) |
| 3 | When the estimated LV temperature has been lowered to the target temperature (i.e., at 32.0 degrees C.) |
| 4 through 8 | Every 10 minutes |

Figure 14:
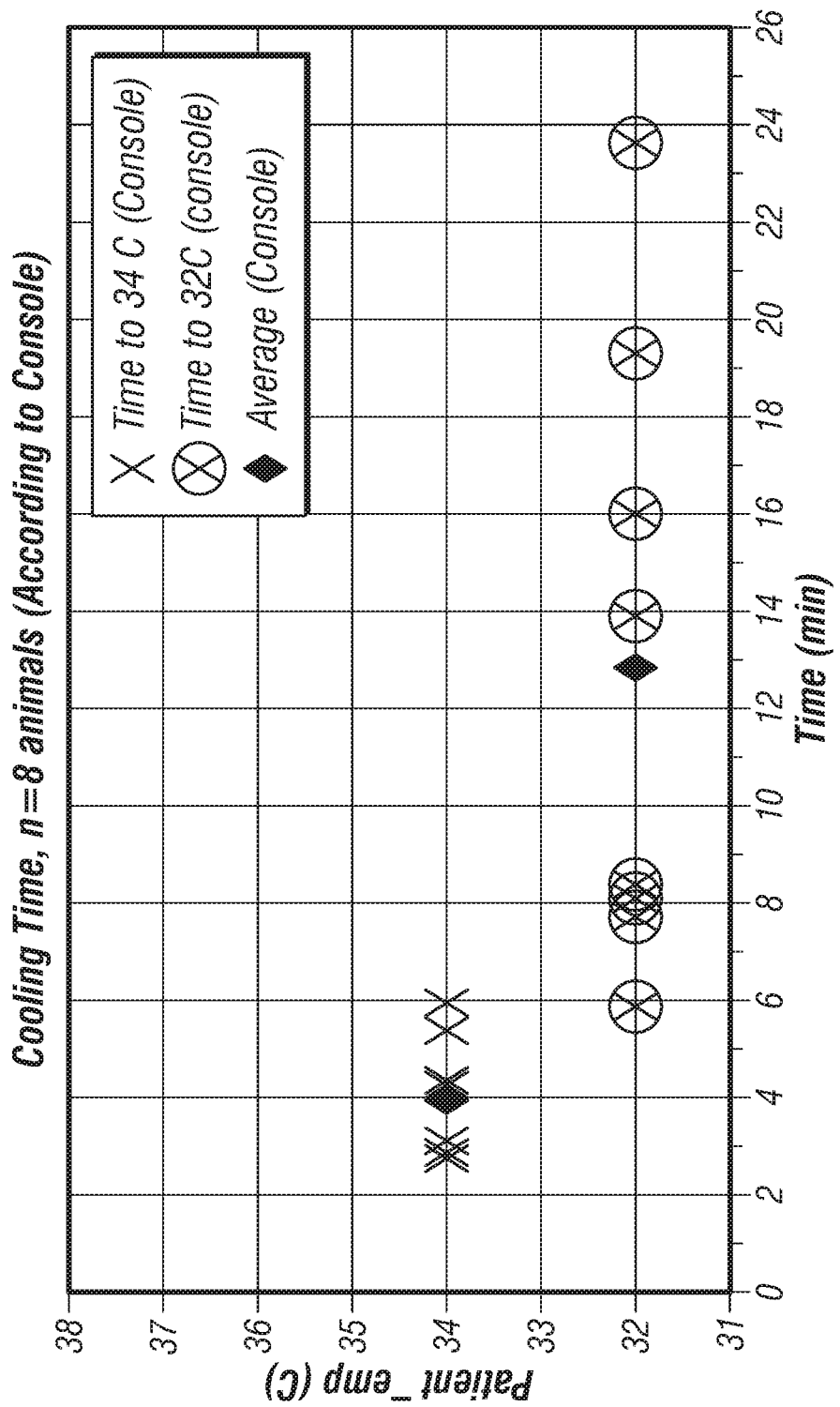
FIG. 14 is a graph of cooling time in pigs in accordance with the example set forth below.

FIG. 14 shows the time it took for the system to cool each animal's estimated left ventricular temperature to 34 degrees C. and 32 degrees C., respectively. As seen in FIG. 14, the system cooled all eight animals from normothermia to 34 degrees C. in less than 6 minutes. The time required to reach the target temperature of 32 degrees was more variable and ranged from less than 6 minutes to just under 24 minutes. However, all eight pigs were cooled to the target temperature of 32 degrees C. in less than 24 minutes.

LV Estimate Error (i.e., the difference between the estimated LV temperature (TempLV) and the actual LV temperature (ActualTempLV) measured by the LV Control Probe) and IVC Error (i.e., the difference between the actual IVC temperature measured by the IVC probe and the actual LV temperature (ActualTempLV) measured by the LV Control Probe) were calculated for each animal at time points three (3) seconds before each pump stop. Table 1 below shows the Mean estimated LV temperature, the Mean actual LV temperature, the Mean actual IVC temperature, Mean LV Estimate Error and Mean IVC Error of the seven (7) animals at each time point before pump stops 1 through 8. These values were obtained using $k_1=0.002$, $L=0$ and calculating $k_2$ as per the formula referenced herein. Values for $k_2$ ranged from 0.0115 to 0.003.

TABLE 1

| | | | LV err | | IVC err | | |
| --- | --- | --- | --- | --- | --- | --- | --- |
| Mean LV est | Mean LV act | Mean IVC | Mean | Std. Dev | Mean | Std. Dev | Power |
| 33.96 | 34.79 | 32.52 | −0.8 | 1.1 | −2.3 | 1.4 | 529.3 |
| 33.17 | 33.32 | 30.61 | −0.2 | 0.4 | −2.4 | 1.4 | 518.4 |
| 32.01 | 32.10 | 29.62 | −0.1 | 0.3 | −2.3 | 1.4 | 440.6 |
| 31.99 | 31.91 | 30.64 | 0.1 | 0.2 | −1.2 | 0.9 | 214.4 |
| 32.25 | 32.27 | 31.60 | 0.0 | 0.2 | −0.7 | 0.7 | 195.8 |
| 32.68 | 32.69 | 32.48 | 0.0 | 0.2 | −0.3 | 0.6 | 142.1 |
| 33.72 | 33.74 | 33.99 | 0.0 | 0.1 | 0.2 | 0.1 | −54.3 |
| 34.23 | 34.51 | 34.15 | 0.0 | 0.7 | 0.3 | 1.5 | −78.2 |

Figure 15:
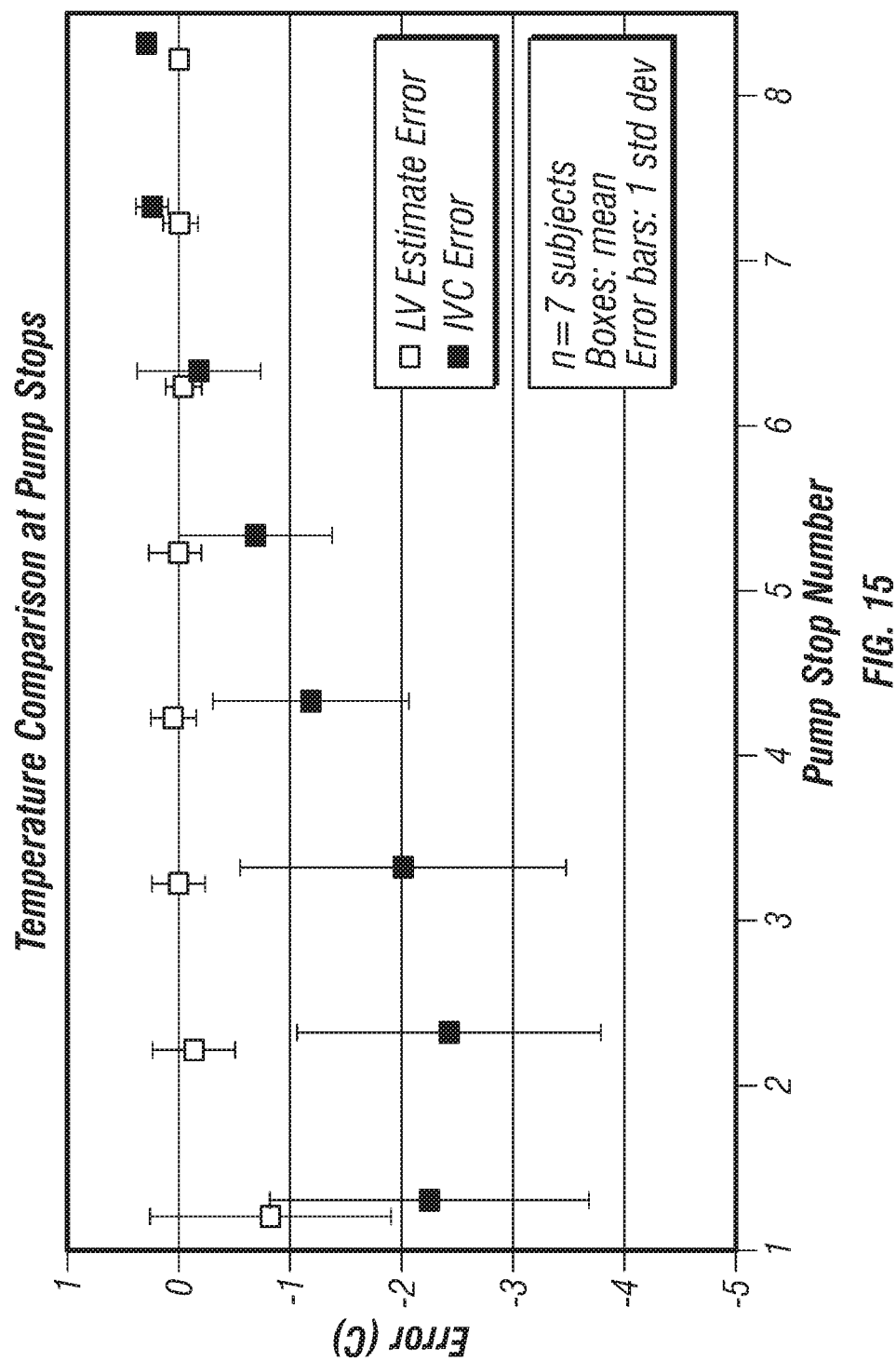
FIG. 15 is a graph showing a comparison of LV Estimate Error (i.e., the difference between directly measured LV temperature and estimated LV temperature) and IVC Error (i.e., the difference between directly measured LV temperature and directly measured IVC temperature) in accordance with the example set forth below.

These data set forth in Table 1 are also shown graphically in FIG. 15. The LV Estimate Error data demonstrates that the estimated LV temperature determined in accordance with this invention consistently provided an accurate and reproducible estimate of actual LV temperature. The Mean LV Estimate Error was near zero for each of the time points preceding Pump Stops 2 through 8. The Mean LV Error for the time point preceding Pump Stop 1 was 0.8+/−1.1. However, that first estimated LV temperature determination was made based solely on the factory pre-set $K_2$ value and does not have the benefit of computed $K_2$ values, as do the later determinations preceding Pump Stops 2 through 8. As described above, in some embodiments of the system, the controller will be programmed not to display estimated LV temperature until the system has performed at least one prior pump stop with at least one prior computation of the $K_2$ value.

The IVC Error data demonstrates that the actual IVC temperature, as measured by the IVC Probe, was substantially different from the actual LV temperature measured by the LV Probe at a number of time points. The IVC Error was greater than the LV Estimate Error at each time point. In this study, the estimated LV Temperature for time points after the first pump stop were accurate and reliable estimates of actual LV temperature as measured by the LV Probe.

The endovascular temperature management system 10 described in various embodiments herein is a high powered system, capable of rapidly cooling a patient.

In certain embodiments, the cassette/console is designed and configured such that it is capable of delivering ≤4° C. working fluid or saline at a rate of ≥600 mL/min, at steady state, when up to 700 W of heat is added to the working fluid or saline loop (e.g., heat added by the subject's body).

In certain embodiments, the cassette/console is designed and configured such that it is capable of delivering ≤4° C. working fluid or saline at a rate of 220+−20 mL/min, at steady state, when ≤70 W of heat is added to the working fluid or saline loop (e.g., heat added by the subject's body).

In certain embodiments, the cassette/console is designed and configured such that it is capable of delivering ≥42° C. working fluid or saline at a rate of >400 mL/min, at steady state, when up to 200 W of heat is removed from the working fluid or saline loop.

In certain embodiments, the system (cassette, console, and catheter) is designed and configured such that it is capable of delivering greater than 400 Watts, or greater than or equal to 500 Watts, or greater than or equal to 600 Watts of cooling power, e.g., with ≤4° C. working fluid or saline at a catheter pressure of about 60 PSI. In certain embodiments, the system may deliver from 500 to 700 W or 600 to 700 W of cooling power or about 675 W of cooling power or greater than 700 W of cooling power.

In certain embodiments, the system (cassette, console, and catheter) is designed and configured such that it is capable of delivering >than or equal to 50 W of warming power e.g., with >37° C. working fluid or saline at a catheter pressure of about 40 PSI.

In certain embodiments, the system performance parameters were verified during a bench test. The bench test included placing a catheter (which is connected to a console/cassette assembly) in a rigid 22 mm ID tube, which simulates the average IVC (inferior vena cava) diameter, through which water at a temperature of 37 degrees C. is flowing at a rate of 2.5 liters per minute (simulating blood flow) over the catheter in a direction from the proximal end of the catheter to the distal end of the catheter.

In certain embodiments, in maintenance and controlled rate warming, the system may control a stable patient's temperature, as measured by console, within about 0.3° C. of target when using a temperature sensor or probe on or in the catheter. During normal use and in the case of a sudden saline loop blockage, the system shall regulate and limit working fluid or saline pressure for catheters as follows: <20 C: 60 psi nominal, 90 psi limit; >=20 C: 40 psi nominal, 70 psi limit; or 40 psi nominal, 70 psi limit. The console working fluid pump and cassette shall be capable of an output up to 600 mL/min at 70 psi. Saline or working fluid pressure at the outlet of the saline pump may be measured, e.g., over a range of 0-100 psi with an accuracy of ±5 psi over the range 10-70 psi. The system may be used concurrently with a defibrillator, electro surgical unit or other device or during an MRI. The console and cassette together may be capable of delivering <8° C. saline, at a rate of ≥600 mL/min, within 5 minutes of turning on the console, when starting with the system equilibrated to ambient temperature. The console and cassette together may be capable of changing the temperature from 4° C. to 40° C. within 10 minutes.

The estimated target temperature, estimated or calculated in accordance with the embodiments described herein, provides feedback to the console, which in turn increases, decreases or maintains cooling/warming power of the system based on the feedback. The proximity of the temperature sensor to the catheter may determine how accurately the sensor is able to measure the patient temperature since the catheter power output influences the measured temperature. The catheter power output is first transferred to the patient via the blood that comes into contact with the catheter and it is slowly diffused across the patient via blood flow, conduction and other processes. If the temperature sensor measures the blood temperature prior to the diffusion being complete, it may indicate a lower than normal patient temperature. For the endovascular temperature management system 10, described herein, the power output may be large enough to cause such discrepancies between the actual patient temperature and the temperature measured by the temperature sensor at the end of the catheter. As a result, an estimation algorithm may be used in order to account for the power output of the catheter influencing the temperature measured by the sensor. The estimated temperature of a target location, e.g., the left ventricle, may be used as a surrogate for body temperature or core body temperature.

In at least some cases where hypothermia is being induced for therapeutic or prophylactic purposes, the speed with which the patient is cooled may be critical. For example, discussed above, at least in acute myocardial infarction (AMI) cases, lowering of the patient's core body temperature to at least 35° C. prior to reperfusion of the ischemic myocardium may have beneficial effects. In some hospitals reperfusion may be accomplished as quickly as 30 to 60 minutes after the patient's arrival at the facility. Thus, to effectively treat myocardial infarction patients, it is desirable for the hypothermia system to have enough power to cool the patient to a desired hypothermic temperature between 32 to 34 degrees C. in less than 30 minutes, e.g., in about 25 minutes or less or 20 minutes or less. However, such rapid cooling is not without risks. Rapid cooling, if not properly controlled, may result in overshoot of the intended hypothermic temperature in certain organs or areas of the body. For example, atrial fibrillation is believed to be common when the heart is cooled to a temperature below 32 degrees C.

As demonstrated by the above-examples, the embodiment of the system 10 used in the example does, indeed, have sufficient cooling power to cool the body of an adult patient to a temperature of 32-34 degrees C. in less than 20 minutes. However, along with having the power needed for rapid cooling, this system 10 is additionally capable of safeguarding against overcooling or undercooling of the heart by monitoring and controlling the estimated cardiac temperature (i.e., estimated LV temperature) rather than some other "core" body temperature taken at an extra-cardiac location (e.g., in the inferior vena cava, urinary bladder, rectum, etc.). By controlling the rate at which the patient's blood is cooled based on feedback of an estimated cardiac temperature as opposed to some other "core" temperature measurement, the systems described in certain embodiments herein offer precise control of cardiac cooling to but not below a particular hypothermic temperature (e.g., 32 degrees C.). This novel combination of therapeutic cooling power with feedback control based on a monitored cardiac temperature estimate is particularly useful in the rapid treatment of emergent disorders (e.g., acute myocardial infarction) while protecting against inadvertent overcooling of the heart to an arrhythmogenic temperature.

At least some embodiments of the heat exchange catheter system 10 may incorporate processors and user interfaces 38 programmed to provide advanced control and informational features. FIGS. 16 through 22 show screens that appear on the user interface 38 in connection with certain examples of such advanced control and informational features in accordance with the example set forth below.

Figure 16:
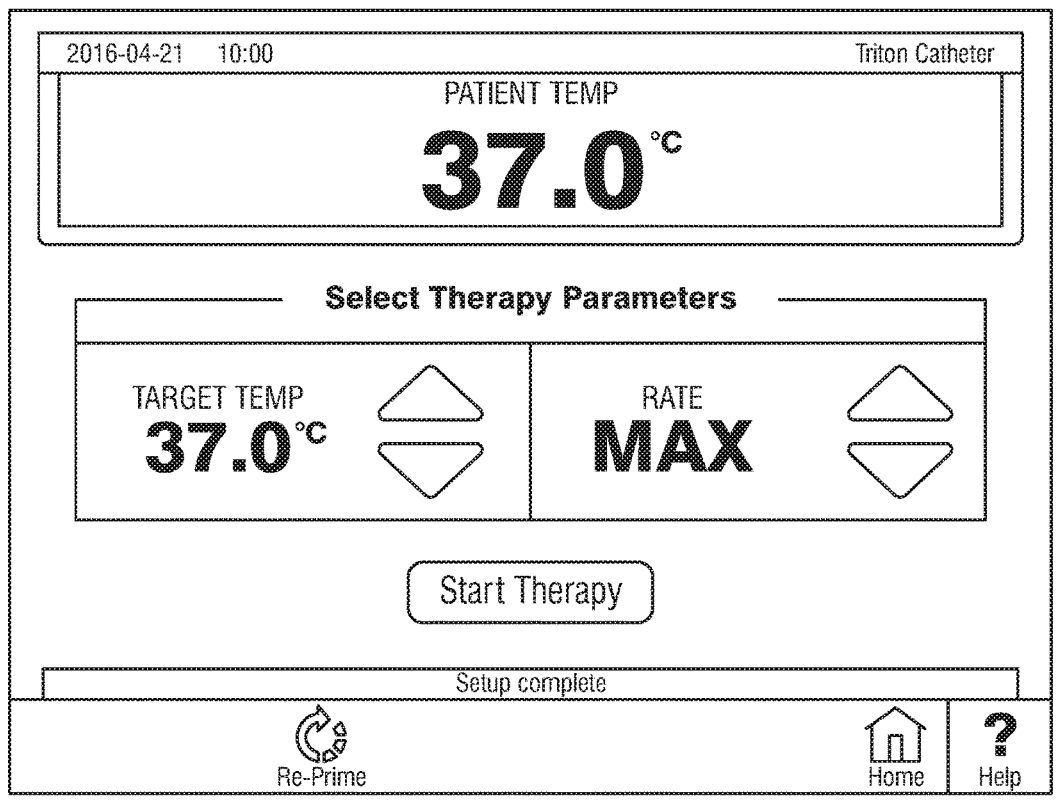
FIG. 16 shows an example of a Modify Therapy Screen which may appear on the user interface of the system of FIG. 1.

FIG. 16 shows an example of a Modify Therapy Screen which may appear on a touch screen embodiment of the user interface 38 of the system 10 of FIG. 1. This screen enables a user to modify the body temperature control protocol being used to treat a particular subject.

Figure 17:
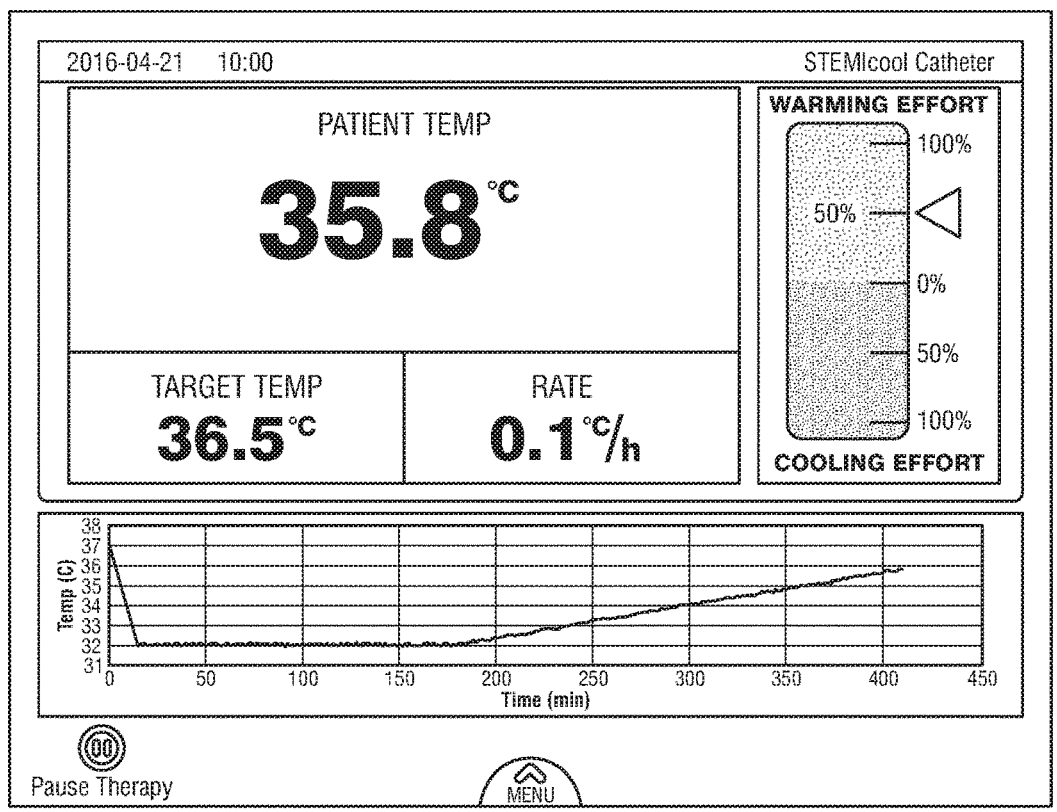
FIG. 17 shows an example of an Operation Screen which may appear on the user interface of the system of FIG. 1

FIG. 17 shows an example of an Operation Screen which may appear on the user interface of the system of FIG. 1. The Operation screen shows the current status of therapy, including the following:

Patient Temp shows the patient's intravascular temperature, which is based on the estimated temperature at the target location derived as described herein.

Target Temp and Rate are chosen in the Modify Therapy Settings screen (See Modify Therapy Settings Screen-FIG. 16).

Warming Effort and Cooling Effort shows the percentage of the system's maximum warming or cooling capability currently being expended.

The patient temperature graph shows the temperature over a 450 minute (7.5 hour) time span. The X-axis shows the time, in minutes, and the Y-axis shows patient's temperature.

To open the Operation menu, press the menu arrow at the bottom of the operation screen.

In this example, the user interface/screen may display the patient temperature. The patient temperature output may be the estimated LV temperature (TempLV). The estimated LV temperature represents or may be used as a surrogate for patient temperature or core body temperature. The estimated LV temperature may be calculated using any of the various equations described herein. In other implementations, the estimated temperature of another organ or anatomical location, other than the LV, may be used as a surrogate for patient temperature or core body temperature, e.g., the femoral artery, aorta, kidney or liver.

Figure 17A:
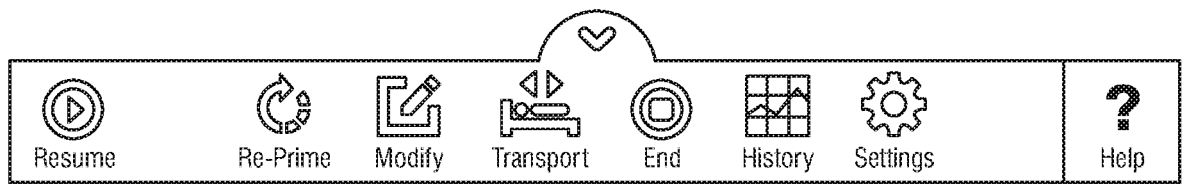
FIG. 17A shows a pop-up menu which appears in response to pushing of the "Menu" icon on the screen shown in FIG. 17.

Pressing the "MENU" icon at the bottom of the Operation Screen will initiate a pop-up Menu display as shown in FIG. 17A. Pressing the "RESUME" icon on the Menu of FIG. 17A will cause the Menu to no longer be visible on the screen and the display will return to the Operation Screen of FIG. 17. As shown, the Menu includes the following icons/functionalities: Menu options are:

Re-Prime-Causes the system 10 to perform a re-priming procedure in which the system is re-filled with saline solution and any entrained air is purged from the system while no therapy is provided. If therapy is paused, press Resume to resume therapy.

Modify—Pressing the Modify icon will bring up the Modify Therapy screen shown in FIG. 16, thereby enabling the user to change the patient's target temperature or rate of cooling/warming during the treatment session.

Transport—Causes the system 10 to pause a treatment session to allow transport or movement of the subject. In certain embodiments, the system may store all treatment session settings and history so that, after the transport has been completed, the user may elect to resume the ongoing treatment session at the point where it has stopped prior to the transport without any change in settings or stored history data.

End—Causes the treatment session to end.

Figure 18:
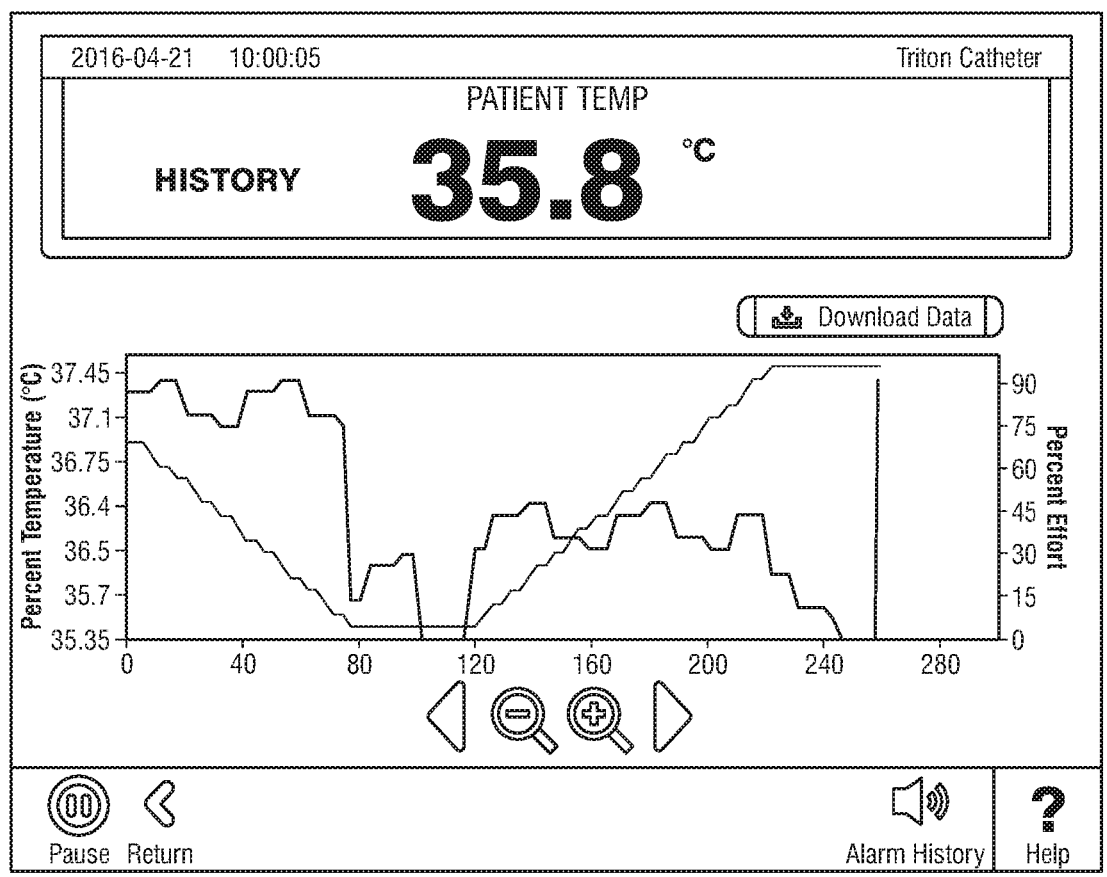
FIG. 18 shows a History Screen which may appear on the user interface of the system of FIG. 1.

History—Pressing the History icon will bring up the History screen shown in FIG. 18, thereby enabling the user to scroll through a graphic display of the entire temperature history and percent effort for the current treatment session. Pressing the + or − icons on any screen where they appear will cause the display to zoom in or out on a specific portion of the information displayed on that screen (see example of zoom feature in FIGS. 19-20).

Figure 22:
FIG. 22 shows a Settings Screen which may appear on the user interface of the system of FIG. 1.

Settings—Pressing the Settings icon will bring up the Settings Screen shown in FIG. 22.

FIG. 18 shows a History Screen which may appear on the user interface of the system of FIG. 1. This screen displays graphic display of the subject body temperature history and percent effort for the current treatment session.

Figure 19:
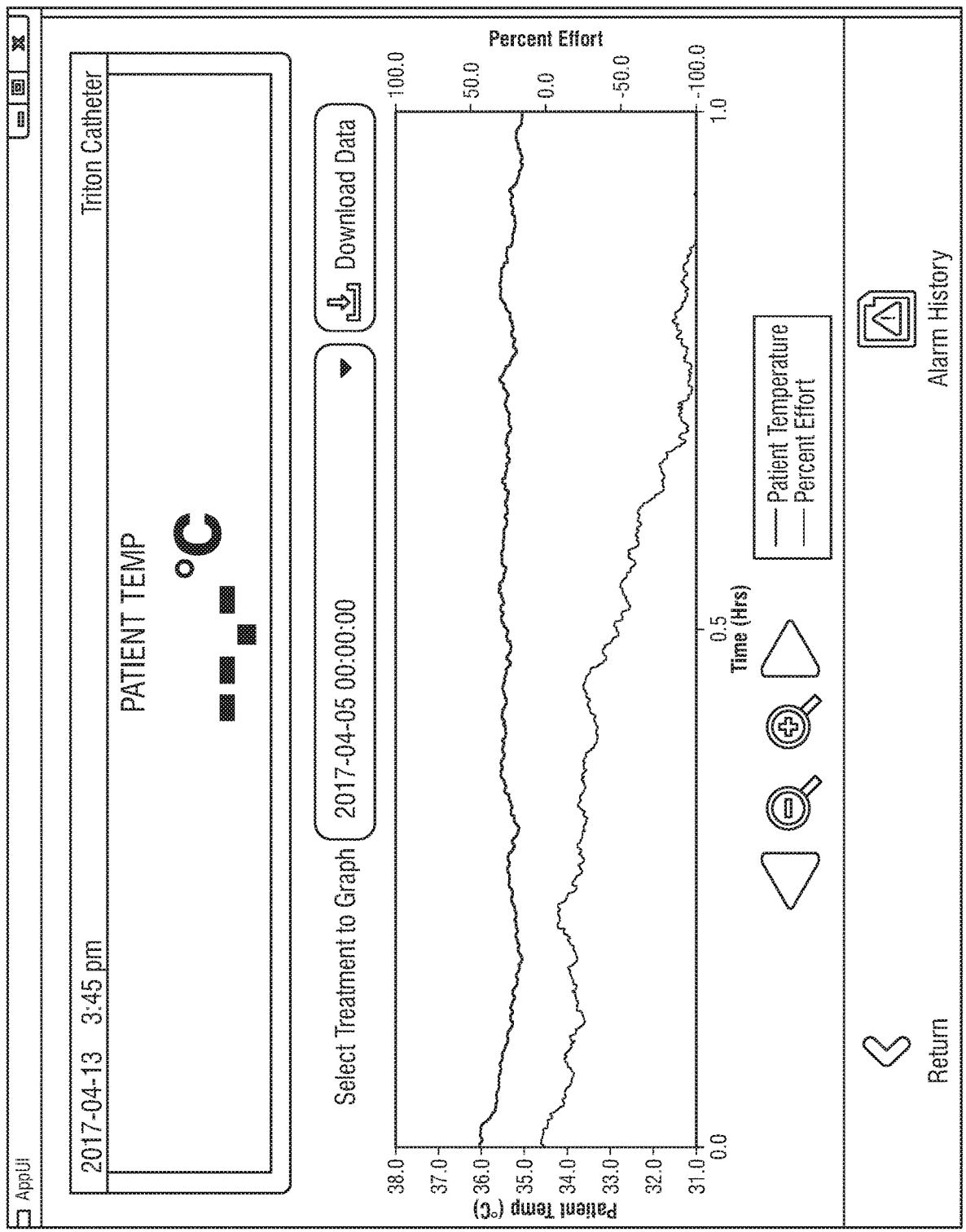
FIG. 19 shows a Patient Temperature Screen which may appear on the user interface of the system of FIG. 1

FIG. 19 shows a Patient Temperature Screen which may appear on the user interface of the system of FIG. 1 This screen provides a graphic display of subject body temperature and percent effort for the preceding one hour.

Figure 20:
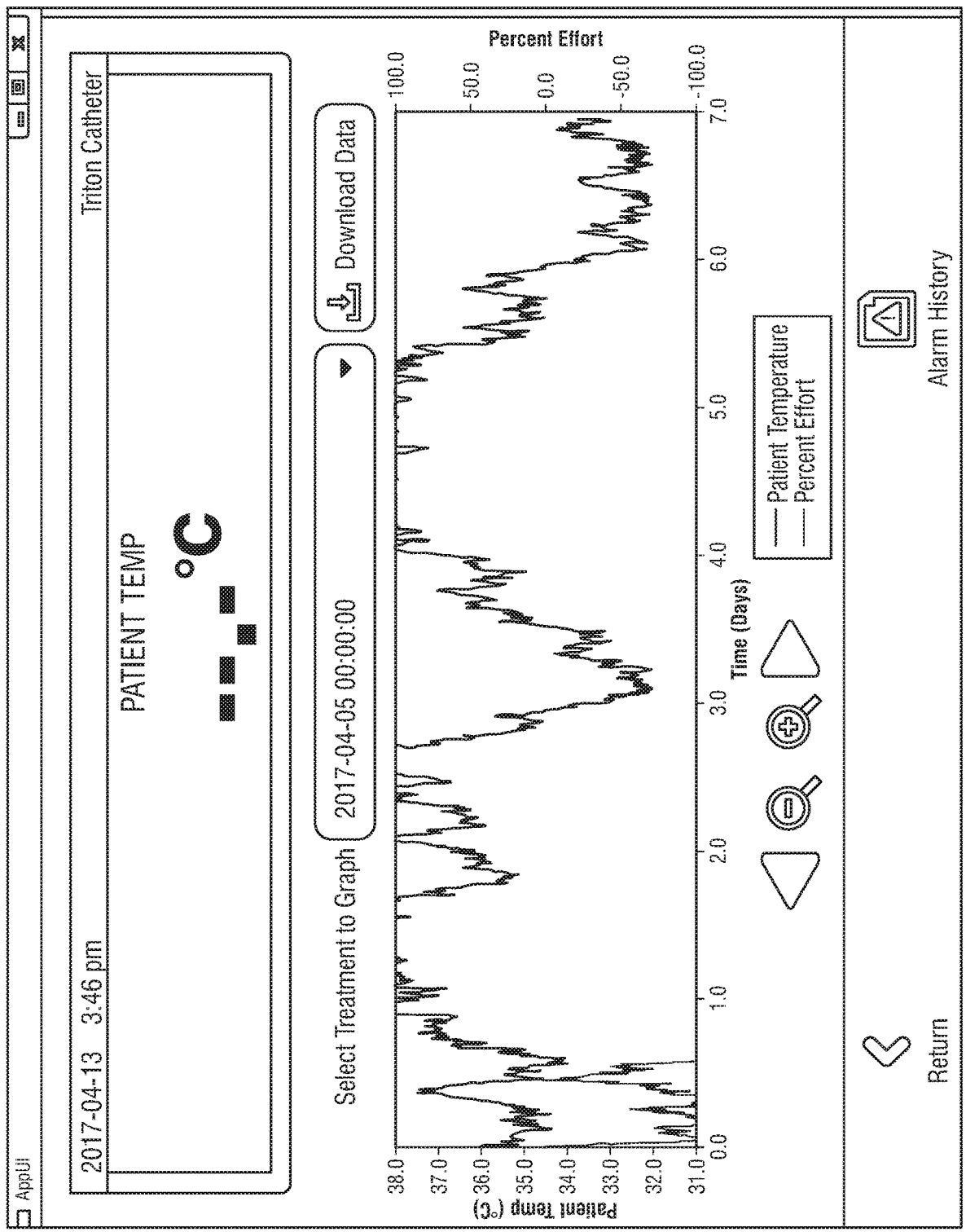
FIG. 20 shows an enlarged "zoom" view of a portion of the graphic displayed on the screen in FIG. 19.

FIG. 20 shows an enlarged "zoom" view of a portion of the graphic displayed on the screen in FIG. 19 accessed by pressing the + icon. Pressing the − icon will cause the display to zoom out and resume the full one hour display seen in FIG. 19.

Figure 21:
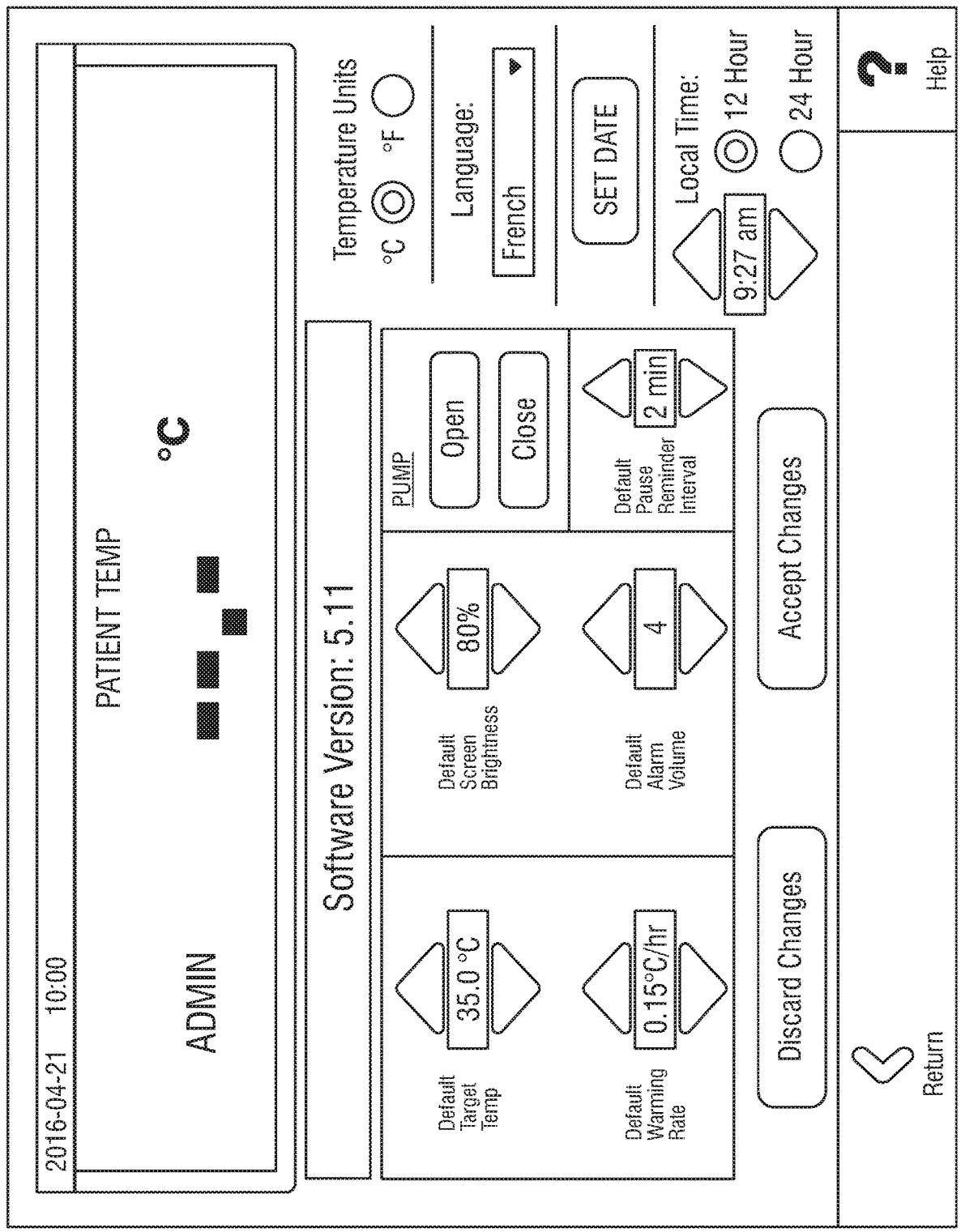
FIG. 21 shows an Administration Screen which may appear on the user interface of the system of FIG. 1

FIG. 21 shows an Administration Screen which may appear on the user interface of the system of FIG. 1. The Admin screen allows you to set the default settings. The Admin screen includes the following:

Default Target Temp

Default Warming Rate. The rate at which the patient is warmed, in degrees per hour.

Default screen brightness

Default Alarm Volume. To test the alarm volume, press the up and down arrows.

Pump. Opens the pump head in case you want to bypass the End therapy procedure and remove the cassette.

Default Pause Reminder Interval.

Temperature Units. Choose to view the temperature in degrees Celsius or Fahrenheit.

Language

Set Date. Press to show a calendar and select the current date.

Local time. Set the time in 12 or 24 hour formats.

FIG. 22 shows a Settings Screen which may appear on the user interface of the system of FIG. 1 to allow operator adjustment of the indicated settings.

In certain embodiments, one or more of the systems described herein may also include one or more physiological alarms and/or technical alarms. The physiological alarms may appear next to the patient's temp on the display screen, and may occur when the patient temperature exceeds the high or low patient temperature alarm value. Technical alarms may appear elsewhere on the display screen and may be triggered by console errors or other events, e.g., probe or catheter disconnection, saline loop overpressure, pump malfunction or open lid, and may be displayed by priority. Any of the alarms may be audible. The system may also transmit data, including patient and/or treatment data wirelessly, e.g., via Wifi, Bluetooth or other wireless connection. Data may also be transmitted via USB, Ethernet or wired connection. The system may be electrically powered or battery powered.

Hypothermic Treatment to Deter Reperfusion Injury

FIG. 23 shows one example of a clinical protocol that may be used to effect rapid hypothermia to deter reperfusion injury in a subject suffering from an ischemic event that may be treated in a manner that causes reperfusion or restoration of blood flow to the ischemic tissue. Non-limiting examples of such reperfursion procedures include angioplasty, stenting, atherectomy, embolectomy, thrombectomy, insertion of a perfusion wire or other conduit to carry blood or oxygenated fluid through or past an obstruction, administration or a thrombolytic agent (e.g., streptokinase or tissue plasminogen activator), some types of surgical revascularization, etc. While reperfusion treatments may restore a flow of blood or other oxygenated fluid to the ischemic tissue, they can also result in significant reperfusion injury which contributes to the amount of tissue that is ultimately infarcted or caused to become necrotic due to the ischemic event. Reperfusion injury is thought to occur in stages. Initially, the ischemia causes increased permeability of capillaries and arterioles. When reperfusion is accomplished, the renewed pressure within those damaged capillaries and arterioles results in diffusion and filtration of fluid into the adjacent tissue. This causes chemical imbalances within the tissue that give rise to an inflammatory response. These events and possibly others result in post-reperfusion damage to the tissue that may be permanent.

As explained herein, the above-described heat exchange catheter system 10 has the unique ability to cool an adult human subject's body to a hypothermic temperature below 34 degrees C., and preferably between 32 degrees C. and 34 degrees C., in approximately 20 minutes. This rapid induction of hypothermia allows caregivers to select an appropriate time to perform the reperfusion procedure after the subjects body temperature has been lowered to the target temperature. Prior studies have indicated that if hypothermia below 35 degrees C. is effected prior to reperfursion, the severity of reperfursion injury, and hence the size or severity of any permanent tissue infarction, is reduced. Applicant has performed a pilot study using the above-described protocol for deterrence of reperfusion injury in human subjects presenting at hospital emergency departments suffering from acute ST elevation myocardial infarction (STEMI). In this pilot study, subjects were randomized into hypothermia and non-hypothermia (control) groups. Subjects in the hypothermia group received standard anti-shivering medication and a heat exchange catheter was placed in the inferior vena cava (IVC). A high power heat exchange catheter system was then used to rapidly cool the body of each subject in the hypothermia group to a temperature below 34 degrees C. within <90 minutes of the subject's arrival in the emergency department. Each subject then underwent percutaneous coronary Intervention (PCI) resulting in reperfusion of the ischemic myocardium. The subjects in the hypothermia group had a body temperatures at the time of reperfusion (i.e., measured at PCI wire crossing) of 33.6+1.0 degrees C.

Following completion of the reperfusion procedure, hypothermia was maintained in each hypothermia group subject for a period of three hours at a target temperature setting of 32 degrees C. Thereafter, the hypothermia group subjects were gradually rewarmed to a body temperature of 36 degrees C. at a rate of 1 degrees C. per hour.

Four to six days after the event, each subject underwent cardiac magnetic resonance imaging (cMR) and infarct size divided by left ventricular mass (IS/LVM) was determined. On average, subjects in the hypothermia group had a 7.1% absolute change in IS/LVM and approximately a 30% relative reduction compared to the non-hypothermia controls. A 5% absolute change in IS/LVM is generally viewed as a good clinical outcome.

The results of this pilot study, when compared with previously reported data, suggests that 1) cooling of the subject's body temperature at a faster rate (i.e., made possible by using a high cooling power system) results in reduced infarct size measured as IS/LVM, 2) There appears to be a dose-response relationship whereby lower body temperature at the time of reperfusion correlates with greater protection against reperfusion injury and, thus, smaller infarct size.

Accordingly, a method for reducing reperfusion injury in a human or animal subject who undergoes a reperfusion procedure following an ischemic event (e.g., myocardial infarction, acute coronary syndrome, stroke, infarction or ischemia of any metabolic tissue or organ including but not limited to heart, lung, kidney, liver and brain) is provided. In this method, the heat exchange catheter 12 is inserted into the subject's vasculature and the system 10 is used to lower a body temperature of the subject to a temperature below 34 degrees C. and preferably between 32 degrees C. and 34 degrees C. prior to reperfusion. The above described techniques for estimating body temperature at a target location may be utilized in this method and the target location may be in or near the organ or tissue where the ischemia is occurring. For example, in a subject suffering from an evolving myocardial infarction of myocardial ischemia, the system 10 may operate to lower the estimated cardiac temperature (LV Temperature) to the hypothermic temperature. Thereafter, caregivers may perform a reperfusion procedure at a selected time after the body temperature has been cooled to the target hypothermic temperature, thereby deterring reperfusion injury and/or reducing the amount of tissue that ultimately becomes infarcted or necrotic.

It is to be appreciated that, in some applications or embodiments described herein, the intent may be to effect whole body cooling and/or warming to control the patient temperature or core body temperature of the subject and, in those applications or embodiments, the estimated temperature at the target location may be used as an indication or surrogate for the subject's core body temperature. In other application or embodiments, the intent may be to effect selective warming or cooling of a particular organ or area of the subject's body and, in those applications or embodiments, the estimated temperature at the target location may be used to effect precise control of the local temperature of that particular organ or area of the subject's body even though, depending on where the heat exchange catheter(s) is/are positioned and how the heat exchange catheter(s) is/are used, there may or may not also be incidental warming or cooling of the subject core body temperature. In the examples where estimated left ventricular temperature (TempLV) is used, such temperature has been determined to not only be an indicator of local cardiac temperature but also a reliable indicator of or surrogate for the subject's body temperature or core body temperature.

It is to be further appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims.

What is claimed is:

1. A system for warming or cooling a subject to a target temperature, said system comprising:
    a heat exchanger configured to exchange heat with the subject's flowing blood at a heat exchange location upstream or downstream of a target location;
    a temperature sensor configured to sense a temperature of the subject's flowing blood at a temperature sensing location, which is upstream or downstream from the target location; and
    a controller configured to:
        receive one or more signals from the temperature sensor indicating the temperature of the subject's flowing blood being sensed at the temperature sensing location;
        determine a heating or cooling power output of the heat exchanger, the heating or cooling power output being transferred to the subject from the heat exchanger;
        determine a change in temperature of the temperature sensing location per unit of heating or cooling power output of the heat exchanger;
        estimate the temperature at the target location, based on the heating or cooling power output of the heat exchanger, the change in temperature of the temperature sensing location per unit of heating or cooling power output of the heat exchanger, and the temperature sensed at the temperature sensing location; and
        based on the estimated temperature at the target location, control the heat exchanger to warm or cool blood flowing through the heat exchange location as needed to result in warming or cooling of the target location to the target temperature.

2. A system according to claim 1, wherein the target location is within a left ventricle of a heart of the subject, the heat exchange location is within an inferior vena cava or superior vena cava of the subject, and the temperature sensing location is in a vasculature of the subject downstream of the heat exchange location.

3. A system according to claim 2, wherein the controller is configured to estimate a temperature within the left ventricle of the heart of the subject by estimating based on a temperature sensed in the inferior vena cava and at least in part on a change in the left ventricle temperature calculated as a function of the heating or cooling power output of the heat exchanger over time and a change in inferior vena cava temperature calculated as a function of the heating or cooling power output of the heat exchanger over time.

4. A system according to claim 3, wherein the controller is configured to estimate the temperature within the left ventricle by estimating based additionally on a predetermined difference in blood temperature between the left ventricle and inferior vena cava.

5. A system of claim 1, wherein the controller is configured to adjust the heating or cooling power output of the heat exchanger based on the estimated temperature at the target location.

6. A system according to claim 1, wherein both the heat exchange location and the temperature sensing location are in an inferior vena cava (IVC) of the subject and the target location is in a left ventricle (LV) of a heart of the subject, and wherein the controller is programmed to estimate temperature at the target location within the left ventricle using a formula comprising:

$$TempLV = IVC + (K2-K1) \cdot Power$$

Wherein:
TempLV is the estimated temperature at the target location within the left ventricle;
IVC is a current sensed temperature at the temperature sensing location;
K1 is a constant which represents a change in LV Temperature per Watt of the heating or cooling power output of the heat exchanger;
K2 is a constant which represents a change in IVC temperature per Watt of the heating or cooling power output; and
Power is the heating or cooling power output of the heat exchanger.

7. A system according to claim 6, wherein K1 is calculated based on experimental or historical data.

8. A system according to claim 6, wherein K1 is calculated using a formula comprising:

$$K1 = K2 \cdot CK \text{ ratio}$$

wherein CK ratio is a ratio of K1 to K2 determined based on experimental or historical data.

9. A system according to claim 6, wherein the controller is pre-programmed with a value for K1.

10. A system according to claim 6, further comprising a pump which pumps heat exchange fluid through the heat exchanger, wherein a pumping of said heat exchange fluid through the heat exchanger is stopped periodically or occasionally and K2 is calculated at each pump stop using a formula comprising:

$$\frac{IVC_{At\ X\ sec\ into\ pump\ stop} - IVC_{Before\ pump\ stop}}{Power_{Before\ pump\ stop}}.$$

11. A system according to claim 6, wherein a heat exchange fluid is pumped through the heat exchanger and the heating or cooling power output is determined as:

Power (Watts) = (HE Fluid Temp OUT − HE Fluid Temp IN) · Flow Rate · CP wherein:
HE Fluid Temp IN is a current measured temperature of heat exchange fluid flowing into the heat exchanger;
HE Fluid Temp OUT is a current measured temperature of heat exchange fluid flowing out of the heat exchanger;
Flow Rate is the measured or calculated flow rate of heat exchange fluid through the heat exchanger; and
CP is a specific heat capacity of the heat exchange fluid.

12. A system according to claim 6, further comprising a pump which pumps heat exchange fluid through the heat exchanger, wherein a pumping of said heat exchange fluid through the heat exchanger is stopped periodically or occasionally and wherein the controller is programmed to perform steps comprising:
calculating and recording the heating or cooling power output before a pump stop;
recording IVC before said pump stop; effecting said pump stop;
recording IVC at x seconds into said pump stop;
calculating a new K2 value if the heating or cooling power output recorded before said pump stop is greater than a predetermined threshold value; and
applying the new K2 value, if calculated, for subsequent LV calculation.

13. A system according to claim 6, further comprising a pump which pumps heat exchange fluid through the heat exchanger, wherein a pumping of said heat exchange fluid through the heat exchanger is stopped periodically or occasionally and wherein controller is programmed to perform steps comprising:
calculating and recording the heating or cooling power output before a pump stop;
recording IVC before said pump stop; effecting said pump stop;
recording IVC at x seconds into said pump stop;
if the heating or cooling power output recorded before said pump stop is greater than a predetermined threshold value, calculating new K1 and K2 values; and
applying the new K1 and K2 values, if calculated, for subsequent TempLV calculation.

14. A system according to claim 6, further comprising a pump which pumps heat exchange fluid through the heat exchanger wherein the controller is programmed to perform steps comprising:
calculating and recording the heating or cooling power output before a pump stop of the pump;
recording IVC before said pump stop;
effecting said pump stop;
recording IVC at x seconds into said pump stop;
if the heating or cooling power output recorded before said pump stop is greater than a predetermined threshold value, calculating a new K2 value; and
if a new K2 value has been calculated, calculating a running average, median or filtered K2 value based on the new K2 value and one or more previous K2 values and, thereafter, using said running average, median or filtered K2 value for LV calculation.

15. A system according to claim 1, wherein both the heat exchange location and the temperature sensing location are in an inferior vena cava (IVC) of the subject and the target location is in a left ventricle (LV) of a heart of the subject; and wherein the controller is programmed to estimate temperature at the target location within the left ventricle using a formula comprising:

$$TempLV = IVC + (K2-K1) \cdot Power + L,$$

wherein:
L is a constant which represents an expected change in the temperature of blood as it circulates through a right portion of a heart and lungs of the subject;
IVC is a current sensed temperature at the temperature sensing location;
K1 is a constant which represents a change in LV Temperature per Watt of the heating or cooling power output of the heat exchanger;
K2 is a constant which represents a change in IVC temperature per Watt of the heating or cooling power output; and
Power is the heating or cooling power output of the heat exchanger.

16. A system for warming or cooling a target location in a body of a subject to a target temperature, said system comprising:
- a heat exchange catheter having a heat exchanger, said heat exchange catheter being insertable into a vasculature of the subject such that the heat exchanger is positioned at a heat exchange location within the vasculature of the subject;
- a heater/cooler apparatus for alternately warming or cooling a heat exchange medium;
- inflow and outflow conduits connecting the heater/cooler apparatus to the heat exchange catheter;
- a pump for repeatedly circulating heat exchange fluid from the heater/cooler apparatus, through the inflow conduit, into the heat exchange catheter, through the heat exchanger, out of the heat exchange catheter, through the outflow conduit and back into the heater/cooler apparatus,
- a temperature sensor that is positionable at a temperature sensing location within the subject's vasculature; and
- a controller which receives signals from the temperature sensor indicating blood temperature at the temperature sensing location;
- wherein the controller is configured to:
  - determine a heating or cooling power output of the heat exchanger, the heating or cooling power output being transferred to the subject from the heat exchanger;
  - determine a change in temperature of the temperature sensing location per unit of heating or cooling power output of the heat exchanger;
  - estimate the temperature at the target location based on the heating or cooling power output of the heat exchanger, the change in temperature of the temperature sensing location per unit of heating or cooling power output of the heat exchanger, and the temperature sensed at the temperature sensing location; and
  - control the temperature and/or a flow rate of the heat exchange fluid to cause the estimated temperature at the target location to rise or fall to the target temperature.

17. A system according to claim 16, wherein both the heat exchange location and the temperature sensing location are in an inferior vena cava (IVC) of the subject and the target location is in a left ventricle (LV) of a heart of the subject, and wherein the controller is programmed to estimate a temperature at the target location within the left ventricle using a formula comprising:

TempLV=IVC+(K2−K1)·Power wherein:
TempLV is the estimated temperature at the target location within the left ventricle;
IVC is a sensed temperature at the temperature sensing location;
K1 is a constant which represents a change in LV Temperature per Watt of the heating or cooling power output of the heat exchanger;
K2 is a constant which represents a change in IVC temperature per Watt the heating or cooling power output; and
Power is the heating or cooling power output of the heat exchanger.

18. A system according to claim 17, wherein K1 is calculated using a formula comprising:

K1=K2·CK ratio wherein CK ratio is a ratio of K1 to K2 determined based on experimental or historical data.

19. A system according to claim 17, further comprising a pump which pumps heat exchange fluid through the heat exchanger, wherein a pumping of said heat exchange fluid through the heat exchanger is stopped periodically or occasionally and K2 is calculated at each pump stop using a formula comprising:

$$\frac{IVC_{At\ X\ sec\ into\ pump\ stop} - IVC_{Before\ pump\ stop}}{Power_{Before\ pump\ stop}}.$$

20. A system according to claim 17, wherein Power is determined as:

Power (Watts)=(HE Fluid Temp OUT−HE Fluid Temp IN)·Flow Rate·CP

HE Fluid Temp IN is a current measured temperature of heat exchange fluid flowing into the heat exchanger;
HE Fluid Temp OUT is the current measured temperature of heat exchange fluid flowing out of the heat exchanger;
Flow Rate is the measured or calculated flow rate of heat exchange fluid through the heat exchanger; and
CP is a specific heat capacity of the heat exchange fluid.

21. A system according to claim 16, wherein both the heat exchange location and the temperature sensing location are in an inferior vena cava of the subject and the target location is in left ventricle of a heart the subject, and wherein the controller is programmed to estimate temperature at the target location within the left ventricle using a formula comprising:

TempLV=IVC+(K2−K1)·Power+L, wherein:
L is a constant which represents an expected change in the blood temperature of blood that circulates through a right portion of the heart and lungs;
IVC is a current sensed temperature at the temperature sensing location;
K1 is a constant which represents a change in LV Temperature per Watt of the heating or cooling power output of the heat exchanger;
K2 is a constant which represents a change in IVC temperature per Watt of the heating or cooling power output; and
Power is the heating or cooling power output of the heat exchanger.

* * * * *

UNITED STATES PATENT AND TRADEMARK OFFICE
CERTIFICATE OF CORRECTION

| | | |
|---|---|---|
| PATENT NO. | : 11,497,648 B2 | Page 1 of 1 |
| APPLICATION NO. | : 15/594539 | |
| DATED | : November 15, 2022 | |
| INVENTOR(S) | : Jeremy Thomas Dabrowiak and Gary A. Freeman | |

It is certified that error appears in the above-identified patent and that said Letters Patent is hereby corrected as shown below:

In the Drawings

Sheet 21 of 22, FIG. 23, delete "2SmL/" and insert --25mL/--
Sheet 22 of 22, FIG. 23 (Cont.), Line 11, delete "I.0" and insert --1.0--

In the Specification

Column 2, Line 62, delete "cava"; insert --cava.--
Column 3, Line 44, delete "1"; insert --1.--
Column 3, Line 50, delete "1"; insert --1.--
Column 3, Line 54, delete "1"; insert --1.--
Column 4, Line 15, delete "IVC"; insert --SVC--
Column 10, Line 5, delete "CKration"; insert --CK ratio--
Column 13, Line 4, delete "Swan-Gantz"; insert --Swan-Ganz--
Column 13, Line 24, delete "liver"; insert --liver.--
Column 14, Line 67, delete "jugular)"; insert --jugular).--
Column 17, Line 55, delete "eating"; insert --heating--
Column 17, Line 63, delete "exchanger"; insert --exchanger.--
Column 20, Line 19, delete "220+-20"; insert --220+/-20--
Column 24, Line 4, delete "reperfursion"; insert --reperfusion--
Column 24, Line 34, delete "reperfursion"; insert --reperfusion--
Column 24, Line 35, delete "reperfursion"; insert --reperfusion--
Column 24, Line 59, delete "1 degrees"; insert --1 degree--

In the Claims

Column 27, Line 14, delete "Wherein:"; insert --wherein:--

Signed and Sealed this
Thirteenth Day of June, 2023

*Katherine Kelly Vidal*
Katherine Kelly Vidal
*Director of the United States Patent and Trademark Office*